(12) United States Patent
Höhnel et al.

(10) Patent No.: US 11,583,860 B2
(45) Date of Patent: Feb. 21, 2023

(54) MICROSTRUCTURED THIN HYDROGEL FILMS

(71) Applicant: Ecole Polytechnique Federale De Lausanne, Lausanne (CH)

(72) Inventors: Sylke Höhnel, Lausanne (CH); Nathalie Brandenberg, Chavannes-Renens (CH); Matthias Lutolf, Tolochenaz (CH)

(73) Assignee: Ecole Polytechnique Federale de Lausanne (EPFL), Lausanne (CH)

( * ) Notice: Subject to any disclaimer, the term of this patent is extended or adjusted under 35 U.S.C. 154(b) by 283 days.

(21) Appl. No.: 15/539,045

(22) PCT Filed: Dec. 22, 2014

(86) PCT No.: PCT/IB2014/067242
§ 371 (c)(1),
(2) Date: Jun. 22, 2017

(87) PCT Pub. No.: WO2016/103002
PCT Pub. Date: Jun. 30, 2016

(65) Prior Publication Data
US 2018/0264465 A1 Sep. 20, 2018

(51) Int. Cl.
B01L 3/00 (2006.01)
C12M 1/32 (2006.01)
(Continued)

(52) U.S. Cl.
CPC .............. B01L 3/5085 (2013.01); C12M 1/32 (2013.01); C12M 3/06 (2013.01); C12M 23/12 (2013.01);
(Continued)

(58) Field of Classification Search
CPC .............. B01L 3/5085; B01L 2300/165; B01L 2300/0893; B01L 2300/0851;
(Continued)

(56) References Cited

U.S. PATENT DOCUMENTS

2010/0015697 A1* 1/2010 Junger .............. B01L 3/502761
435/307.1
2010/0055733 A1* 3/2010 Lutolf .................. C12N 5/0647
435/396
(Continued)

FOREIGN PATENT DOCUMENTS

CN 101827931 A 9/2010
JP WO2013/042360 A1 3/2013
(Continued)

OTHER PUBLICATIONS

Kobel et al. (Methods in Molecular biology, vol. 811, 2012, pp. 101-112, XP009185724 (Year: 2012).*
(Continued)

Primary Examiner — Jill A Warden
Assistant Examiner — Henry H Nguyen
(74) Attorney, Agent, or Firm — Muncy, Geissler, Olds & Lowe, P.C.

(57) ABSTRACT

A device for aggregating cells includes a cavity. The cavity includes a plurality of microwells for receiving at least one cell. Each of the microwells includes a vertical sidewall and a curved bottom. The microwells are made in a hydrogel layer. Each of said microwells has a diameter and an interwell distance between one microwell and another microwell, wherein a ratio for the interwell distance to the diameter is less than or equal to 1/10.

19 Claims, 20 Drawing Sheets

(51) Int. Cl.
    *C12M 3/06* (2006.01)
    *C12M 1/00* (2006.01)
(52) U.S. Cl.
    CPC ............ *C12M 23/16* (2013.01); *C12M 23/20* (2013.01); *B01L 2200/026* (2013.01); *B01L 2200/0668* (2013.01); *B01L 2300/0829* (2013.01); *B01L 2300/0851* (2013.01); *B01L 2300/0893* (2013.01); *B01L 2300/165* (2013.01)
(58) Field of Classification Search
    CPC ..... B01L 2300/0829; B01L 2200/0668; B01L 2200/026; C12M 23/20; C12M 3/06; C12M 1/32; C12M 23/16; C12M 23/12; C12M 1/18
    See application file for complete search history.

(56) References Cited

U.S. PATENT DOCUMENTS

| | | | |
|---|---|---|---|
| 2011/0003389 A1* | 1/2011 | Nakazawa | C12N 5/067 435/305.2 |
| 2011/0183312 A1 | 7/2011 | Huang | |
| 2013/0137155 A1* | 5/2013 | Morgan | C12M 21/08 435/174 |
| 2014/0057280 A1* | 2/2014 | Murthy | B01F 25/431 435/7.1 |
| 2014/0162351 A1 | 6/2014 | Yamamoto et al. | |
| 2014/0227784 A1* | 8/2014 | Ejiri | C12M 23/12 435/402 |

FOREIGN PATENT DOCUMENTS

| | | |
|---|---|---|
| JP | 2014079227 A | 5/2014 |
| KR | 1012829260000 | 7/2013 |
| WO | 2005007796 A2 | 1/2005 |
| WO | 2008106771 A1 | 9/2008 |
| WO | 2010023497 A1 | 3/2010 |

OTHER PUBLICATIONS

Cheng et al. (Lab on a chip 2007, 7, 763-769) (Year: 2007).*
Kobel, et al.; "Fabrication of PEG Hydrogel Microwell Arrays for High-Throughput Single Stem Cell Culture and Analysis," in Nanotechnology in Regenerative Medicine: Methods and Protocols; 2012; pp. 101-112; Humana Press, Clifton, N.J.
Abbott, et al.; "Biology's new dimension," in Nature; Aug. 21, 2013; pp. 870-872; vol. 424; Nature Publishing Group.
Chen, et al.; "Shrinky-Dink Hanging Drops: A Simple Way to Form and Culture Embryoid Bodies," in Journal of Visualized Experiments (13); Mar. 5, 2008; e692, doi:10.3791/692.
Choi, et al.; "Controlled-size embryoid body formation in concave microwell arrays," in Biomaterials; 2010; pp. 4296-4303; vol. 31; Elsevier.
Eiraku, et al.; "Self-organizing optic-cup morphogenesis in three-dimensional culture," in Nature; Apr. 7, 2011; pp. 51-56; vol. 472; Macmillan Publishers Limited.
Giselbrecht, et al.; "3D tissue culture substrates produced by microthermoforming of pre-processed polymer films," in Biomed Microdevices; May 20, 2006; pp. 191-199; vol. 8; Springer Science + Business Media, LLC.
Gobaa, et al.; "Artificial niche microarrays for probing single stem cell fate in high throughput," in Nature Methods; Oct. 9, 2011; pp. 949-955; vol. 8, No. 11; Nature Publishing Group.

Griffith, et al.; "Capturing complex 3D tissue physiology in vitro," in Nature Reviews Molecular Cell Biology; Mar. 1, 2006; pp. 211-224; vol. 7; Nature Publishing Group.
Keller; "In vitro differentiation of embryonic stem cells," in Current Opinion in Cell Biology; 1995; pp. 862-869; vol. 7, Issue 6; Elsevier Ltd.
Lancaster; "Cerebral organoids model human brain development and microcephaly," in Nature; Aug. 28, 2013; pp. 373-379; vol. 379; Macmillan Publishers Limited.
Lee; "Compatibility of Mammalian Cells on Surfaces of Poly(dimethylsiloxane)," in Langmuir; Nov. 19, 2004; pp. 11684-11691; vol. 20, Issue 26; American Chemical Society.
Li, et al.; "Stem Cell Niche: Structure and Function," in Annual Review of Cell and Developmental Biology; Jul. 1, 2005; pp. 605-631; vol. 21; Annual Reviews.
Lin; "Recent advances in three-dimensional multicellular spheroid culture for biomedical research," in Biotechnology Journal; Oct. 17, 2008; pp. 1172-1184; vol. 3, Issue 9-10; John Wiley &Sons, Inc.
Liu; "Quasi-spherical microwells on superhydrophobic substrates for long term culture of multicellular spheroids and high throughput assays," in Biomaterials; Jul. 2014; pp. 6060-6068; vol. 35, Issue 23; Elsevier.
Lutolf; "Synthetic biomaterials as instructive extracellular microenvironments for morphogenesis in tissue engineering," in Nature Biotechnology; Jan. 6, 2005; pp. 47-55; vol. 23 #1; Nature Publishing Group.
Nasu; "Robust Formation and Maintenance of Continuous Stratified Cortical Neuroepithelium by Laminin-Containing Matrix in Mouse ES Cell Culture," in PLoS One; Dec. 31, 2012; vol. 7, Issue 12.
Pampaloni; "The third dimension bridges the gap between cell culture and live tissue," in Nature Reviews Molecular Cell Biology; Oct. 1, 2007; pp. 839-845; vol. 8; Nature Publishing Group.
Ranga, et al.; "3D niche microarrays for systems-level analyses of cell fate," in Nature Communications; Jul. 14, 2014; pp. 4324-4334; vol. 5; Macmillan Publishers.
Rowley; "Alginate hydrogels as synthetic extracellular matrix materials," in Biomaterials; Jan. 1999; pp. 45-53; vol. 20; Elsevier.
Shiku; "Noninvasive measurement of respiratory activity of mouse embryoid bodies and its correlation with mRNA levels of undifferentiation/differentiation markers," in Molecular BioSystems; Aug. 7, 2013; pp. 2701-2711; vol. 9; RSC Publishing.
Smith; "Culture and Differentiation of Embryonic Stem Cells," in Journal of Tissue Culture Methods; Jun. 1991; pp. 89-94; vol. 13, Issue 2; Kluwer Academic Publishers.
Suga; "Self-formation of functional adenohypophysis in three-dimensional culture," in Nature International Journal of Science; Nov. 9, 2011; pp. 57-62; vol. 480; Nature Publishing Group.
Tibbitt et al.; "Hydrogels as Extracellular Matrix Mimics for 3D Cell Culture," in Biotechnology & Bioengineering; Apr. 13, 2009; pp. 655-663; vol. 103; John Wiley & Sons.
Toepke; "PDMS absorption of small molecules and consequences in microfluidic applications," in Lab on a Chip; Oct. 4, 2006; pp. 1484-1486; Issue 12; The Royal Society of Chemistry.
Ungrin; Reproducible, "Ultra High-Throughput Formation of Multicellular Organization from Single Cell Suspension-Derived Human Embryonic Stem Cell Aggregates," in PLoS One; Feb. 13, 2008; vol. 3, Issue 2.
Zhang; "Beyond the Petri dish," in Nature Biotachnology; Feb. 2004; 151-152; vol. 22, #2; Nature Publishing Group.
International Search Report.
Kobel, et al.; Micropatterning of Hydrogels by Soft Embossing; Langmuir Article; Mar. 5, 2009; pp. 8774-8779; American Chemical Society (pp. 2-7 of the attached document).
First Office Action from Japan and Translation.
Second Office Action from Japan and Translation.

* cited by examiner

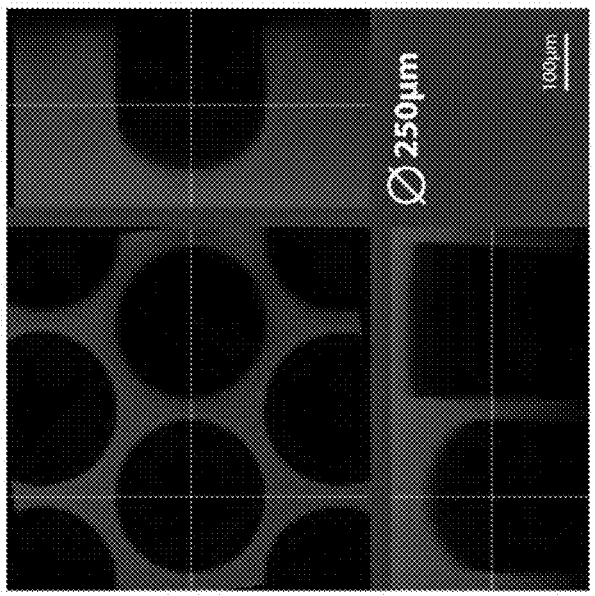
Fig. 8A
Fig. 8B
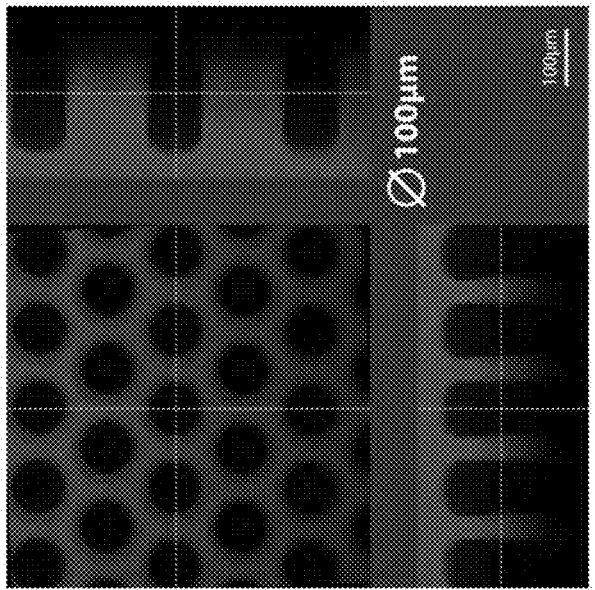
Fig. 8C
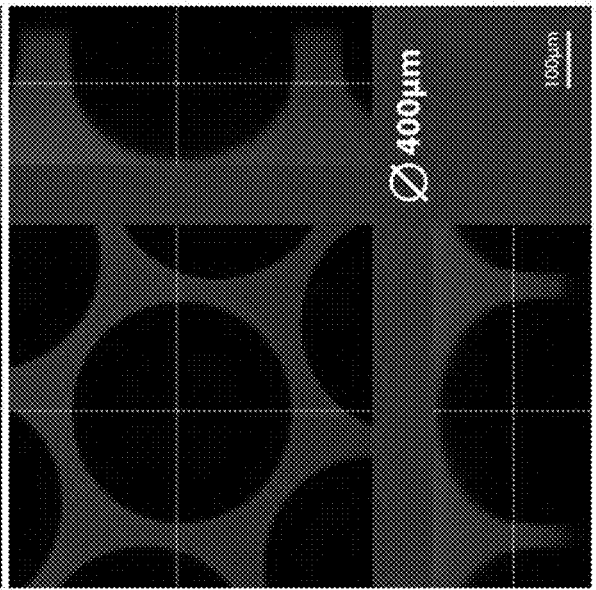
Fig. 8D

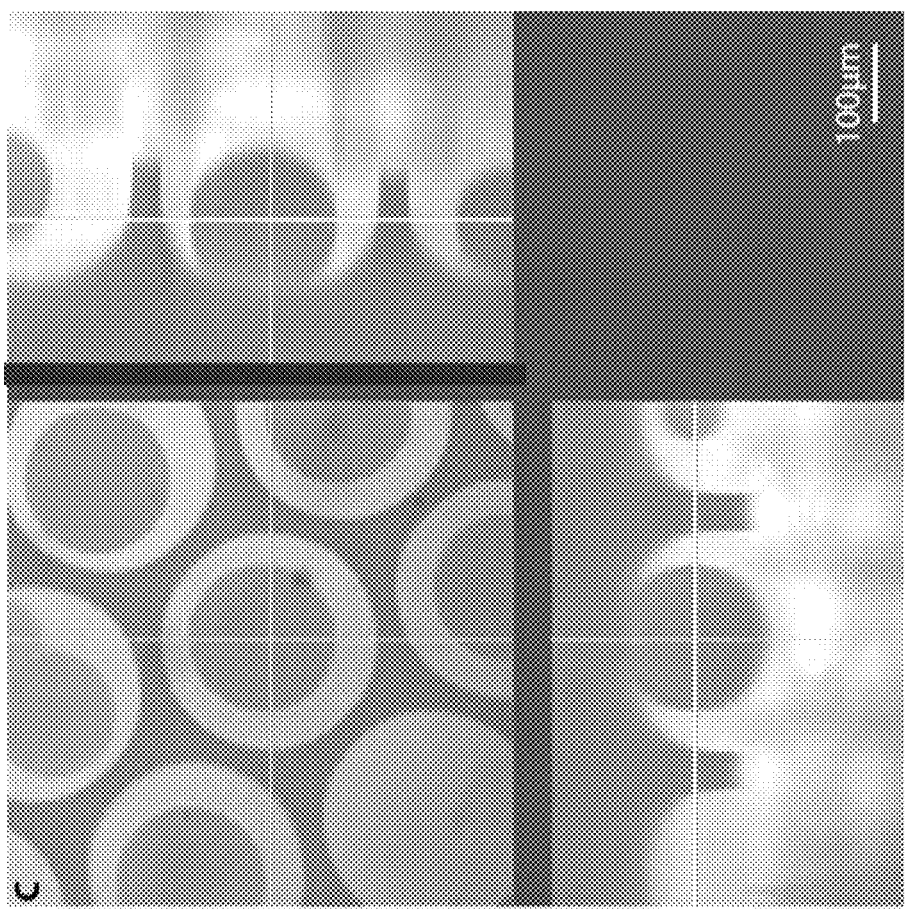
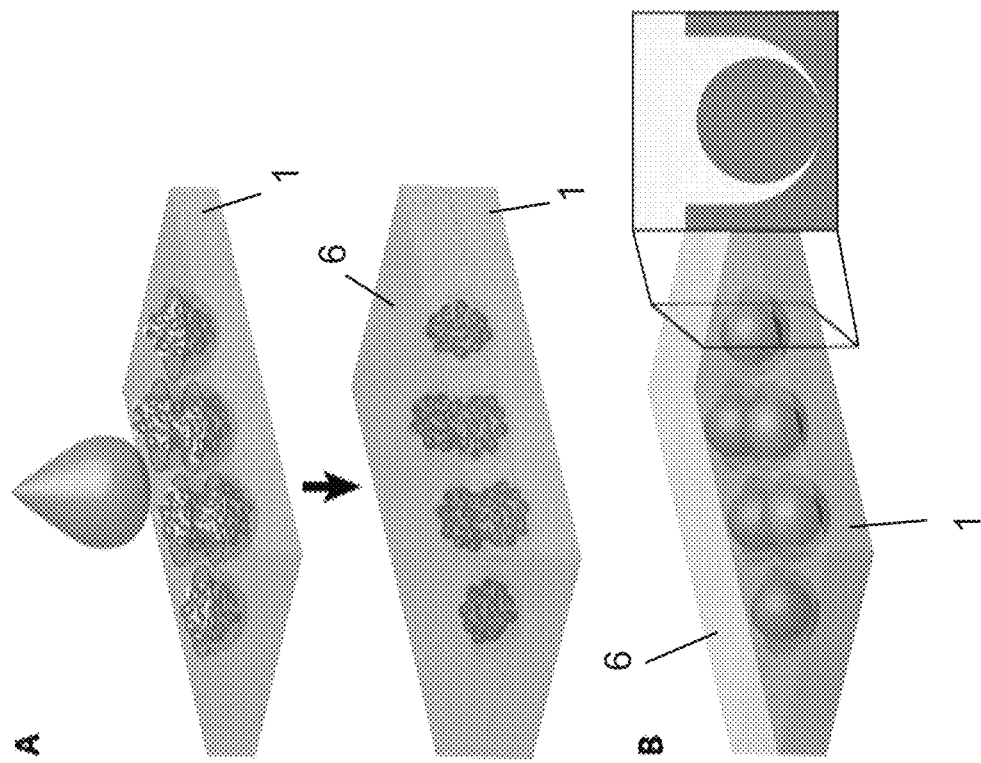
Fig. 17

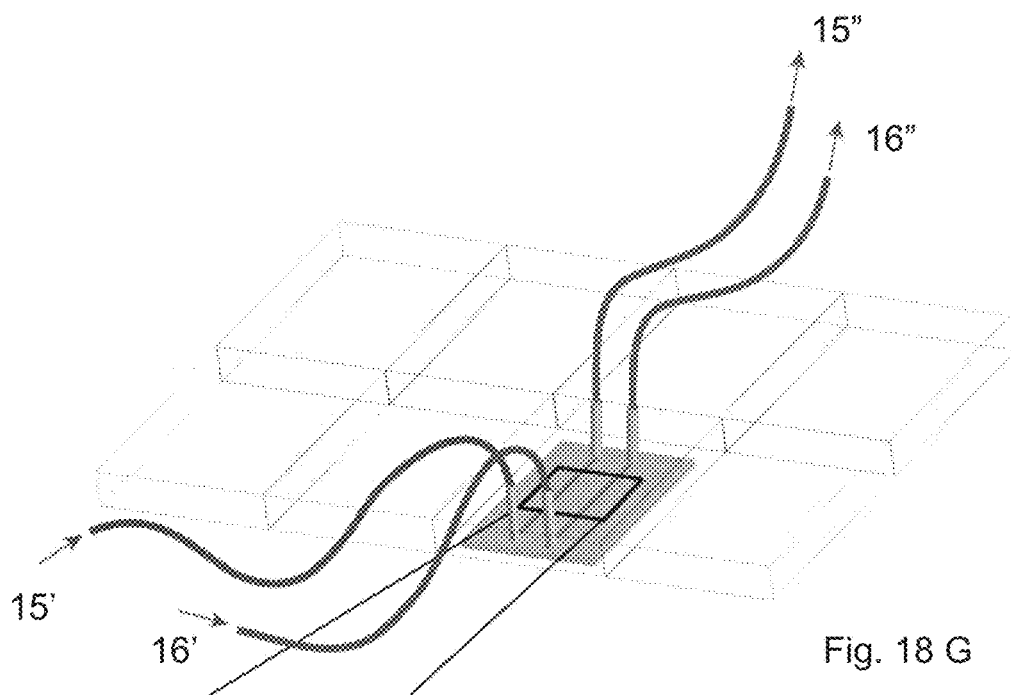
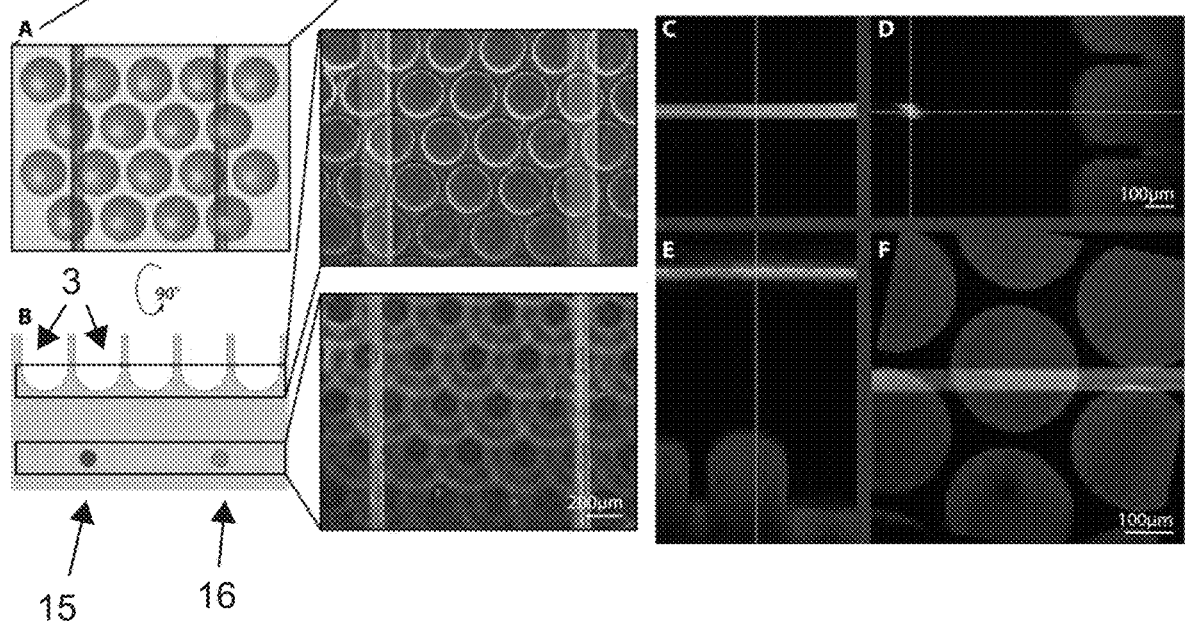
Fig. 18

MICROSTRUCTURED THIN HYDROGEL FILMS

CROSS-REFERENCE TO RELATED APPLICATIONS

This application claims the benefit of PCT Application Number PCT/IB2014/067242, filed Dec. 22, 2014, entitled Devices for High-Throughput Aggregation and Manipulation of Mammalian Cells, which is hereby incorporated by reference in its entirety.

FIELD OF THE INVENTION

The present application relates to devices for high-throughput aggregation of cells and their long-term culture as well as their manipulation within the device. Such cell aggregates are used in basic biology, especially developmental and caner biology, regenerative medicine and pharmaceutical screenings.

The present invention also concerns methods for the fabrication of such devices.

BACKGROUND OF THE INVENTION

Tissues self-organize as complex three-dimensional entities of specialized cells, adjacent support cells, extra-cellular matrix components and other structural and dimensional elements that cross talk continuously to ensure and maintain function (Li et al. 2005). This multicomponent microenvironment, termed niche, has been minimally simplified in classical two-dimensional cell culture systems that serve as standardized platforms for basic research ranging from developmental biology studying the differentiation of cell types of interest to pharmacological screenings of, for example, tumorigenic cells. However results from such two-dimensional assays critically lack the translational aspect back to the three-dimensional in vivo environment (Griffith et al. 2006). As a consequence, experimental designs have been strongly shifting during the past decade towards the implementation of more relevant 3D models, such as cell aggregate cultures (Abbott 2003, Zhang 2004, Pampaloni et al. 2007).

For spheroid formation, hanging drop systems have been established to reliably form cell clusters in a well-controlled manner (Keller 1995). In short, cells are suspended in drops of medium from the lid of a culture plate to induce cell aggregation by gravitational forces. This method is vastly labor-intensive, time-consuming and generally not easily amenable to scalable cultures. While nutrient delivery is ensured to the complete surface of the generated spheroid, medium exchange to enable long-term culture of the aggregates in this format is impossible. Furthermore only a certain range of sizes for cell clusters can be covered with this system (Lin et al. 2008).

Conventional round bottom polystyrene 96-well plates have been introduced into standard biological cell culture for simplified cell aggregation. While this culture format permits a near-natural conformation, i.e. spherical ground cavity, for the production of cell clusters of a wide range of sizes, drawbacks include the difficulty of medium exchange without disturbance of the formed spheroid and still the lack of throughput. Nonetheless 95-well round bottom plates are the most widely used culture format for in vitro organogenesis assays (Eiraku et al. 2011, Suga et al. 2011, Nasu et al. 2012, Lancaster et al. 2013)

To overcome this issue for the field of early developmental biology, a research area where embryonic stem cells are often cultured and differentiated in cell aggregates, a device for the large-scale production of embryonic stem cell clusters has been recently proposed (Ungrin et al. 2008). The device sold as AggreWell™ (STEMCELL Technologies, Canada, PCT/CA08/00397) is advertised as an easy and standardized approach to the reproducible large-scale production of uniform and size-controlled embryonic bodies (EBs). The EBs are generated by centrifuging a cell suspension of defined concentration into a high-density array of pyramidal microwells sized 400 or 800 microns in pyramid-based diameter to initiate cell aggregation within 24 hours. The Aggrewell™800 system indeed harbours microwells with a flat bottom plane, representing a final structure of pyramidal frustums, which partially, if not fully, defeats the purpose of the initial invention of providing a cell collection device where all cells are collected in a central point of summed gravitational forces. Furthermore the system generally exhibits multiple limitations, which render its application for long-term cultures of cell spheroids difficult. Larger sized EBs formed in AggreWell™ plates by either high initial cell seeding density or cell aggregation followed by spheroid growth for longer than 24 h tend to form cone-like structures reflecting the architecture of the AggreWell™ microwell. Constraining cells in non-natural conformations has unknown effects on their biological function and it is currently suggested that shape of the culture substrate can induce uncontrolled and unspecified lineage commitment (Shiku et al. 2013). Moreover, AggreWell™ plates are limited to optimal medium exchange during culture as handling steps such as pipetting disturbs constraint of the spheroids within the microwells due to large openings towards the plane exposed to the bulk medium.

AggreWell' plates are sold as microwell arrays casted in polydimethylsiloxane (PDMS), a silicone elastomer that does not allow nutrient diffusion, which affects growth and survival of cells on the side exposed to PDMS surfaces (Lee et al. 2004). Furthermore, it is well known that PDMS is prone to biomolecule absorption on its surface (Toepke et al. 2006), a factor risking to bias final results of cell signalling and drug screening experiments.

The lack of suitable cell culture substrates is addressed in recent techniques hybridizing biology and material sciences through the application of biocompatible scaffolds such as naturally derived or synthetic hydrogels (Rowley et al. 1999, Lutolf et al. 2005), Tibbitt et al. 2009). Recent technologies have begun to explore the use of such biomaterials for the delivery of bioactive molecules by niche microarrays through flat bottom microwells in 2D (Gobaa et al. 2011) or through 3D scaffolds (Ranga et al. 2014).

There is a need in the art for a method of interfacing reproducible cell aggregation techniques to generate cell spheroids of a single or multiple given cell types with smart functional biomaterials. There is a need in the art to generate these cell aggregates in miniature cavities that imitate geometrical specifications of the formed spheroid and where the geometries are fully customizable to fulfill individual requirements of a given biological system. There is a need in the art to apply all aforementioned requirements to large-scale productions of cellular spheroids in order to provide clinically relevant numbers. There is also a need in the art to allow experimentation and local manipulation of the produced cell aggregates on the same device.

Other prior art publications disclose similar microstructures. For example KR 20130013537 A relates to a manufacturing method of microstructures and a method for cell collecting using said microstructures.

In KR 20130013537 however, the process disclosed has several limitations and disadvantages such as:
- the shape of the well is half sphere or ellipsoid;
- the contact angle at well opening is minimum 20°;
- small wells are impossible to realize;
- the pitch (well-spacing) is identical to the diameter of the wells;
- the material used is limited to PDMS;
- the throughput is limited due to the well spacing (pitch);
- a long term culture is impossible.

SUMMARY OF THE INVENTION

An aim of the present invention is to improve the known cell aggregate systems.

A further aim of the present invention is to propose a system that allows a better tailoring to the need of the user with regards to through-put, size and geometry and interfaces with in situ manipulation techniques.

A further aim is to propose a system that is user-friendly, reproducible and reliable.

A novel family of cell aggregate systems is proposed according to the present invention that will also enable the long-term culture of the formed cellular spheroids within the same culture format.

According to the present invention, a 3D culture system is composed of an array of high-aspect ratio round-bottoms as well as U-bottom shaped microwells with low pitch sizes and high side walls that can be reproduced in various materials not limited to PDMS and other polymeric materials such as plastics, but more importantly hydrogels such as those based on synthetic hydrophilic polymers, preferably poly(ethylene glycol) (PEG), or naturally derived components such as Matrigel, agarose, gelatin or collagens.

To fabricate these arrays, the present invention takes advantage of solvent evaporation of dilute polymer solutions to create round-shaped well as well as U-shaped structures. The round bottom shape is included in the U-bottom shape. Round bottom microwells refer to U-bottom shaped microwells wherein the height of the microwell is equal to the radius of the spherical bottom. Henceforth only the term U-bottom or U-shaped will be used.

The formed U-bottom microwell structures are then molded in the substrate of interest. The advantages of using especially PEG-based hydrogels as substrate materials lie in the high permeability of nutrients, optimal and tailor-made bioactivity while ensuring otherwise biological inertness (Lutolf et al. 2005). Furthermore PEG-based substrates will permit the selective conjugation of desired biomolecules to the bottom of the depicted microwells, allowing the study of also non-soluble factors on cellular behaviour and development within aggregates. By playing on the architecture of the U-bottom microwells, especially the aspect ratio of well depth to diameter, spheroids can be embedded below the surface plane of the culture substrate to minimize disturbance through handling procedures such as movement or medium changes. Minimal pitch sizes in the range of few cell diameters between the wells are sufficient to inhibit single cells to rest on these borders, a process that can disturb equal cell distribution in each well and that can exhibit uncontrolled signalling. Furthermore the integration of microfluidic networks in close proximity to the microwell plane for the local and timed delivery of molecules of interest allows the selective manipulation of the formed aggregates during long-term culture. Additionally, this platform can be applied for complete encapsulation of formed aggregates through sandwich casting of a second layer of substrate atop the formed spheroids, which will allow planar localization and drastically facilitate automated imaging during culture.

Accordingly, the present invention provides a method for generating cell aggregates comprised of one or multiple cell types, through:
(1) Gravitational sedimentation or centrifugation of one or multiple cell types simultaneously.
(2) Gravitational sedimentation or centrifugation of one cell type followed by the addition of another cell type subsequently through gravitational sedimentation at any given time after aggregation of the previous.

In summary the present invention proposes a novel all-in-one 2D and 3D cell culture platform that offers high-throughput formation of cellular spheroids while allowing their long-term culture without need to change culture format while also enabling manipulation of the formed aggregates by local delivery of desired bioactive molecules for functional studies.

BRIEF DESCRIPTION OF THE DRAWINGS

The invention will be better understood from the following description of the drawings in which

FIGS. 8A to 8D illustrate different U-shaped microwell sizes;

FIGS. 17A-C illustrate an example of three-dimensional culture format;

FIGS. 18A-F and enlargement 18 G illustrate an example of U-bottom microwell arrays with microfluidic integration;

DETAILED DESCRIPTION OF THE INVENTION

Figure 1:
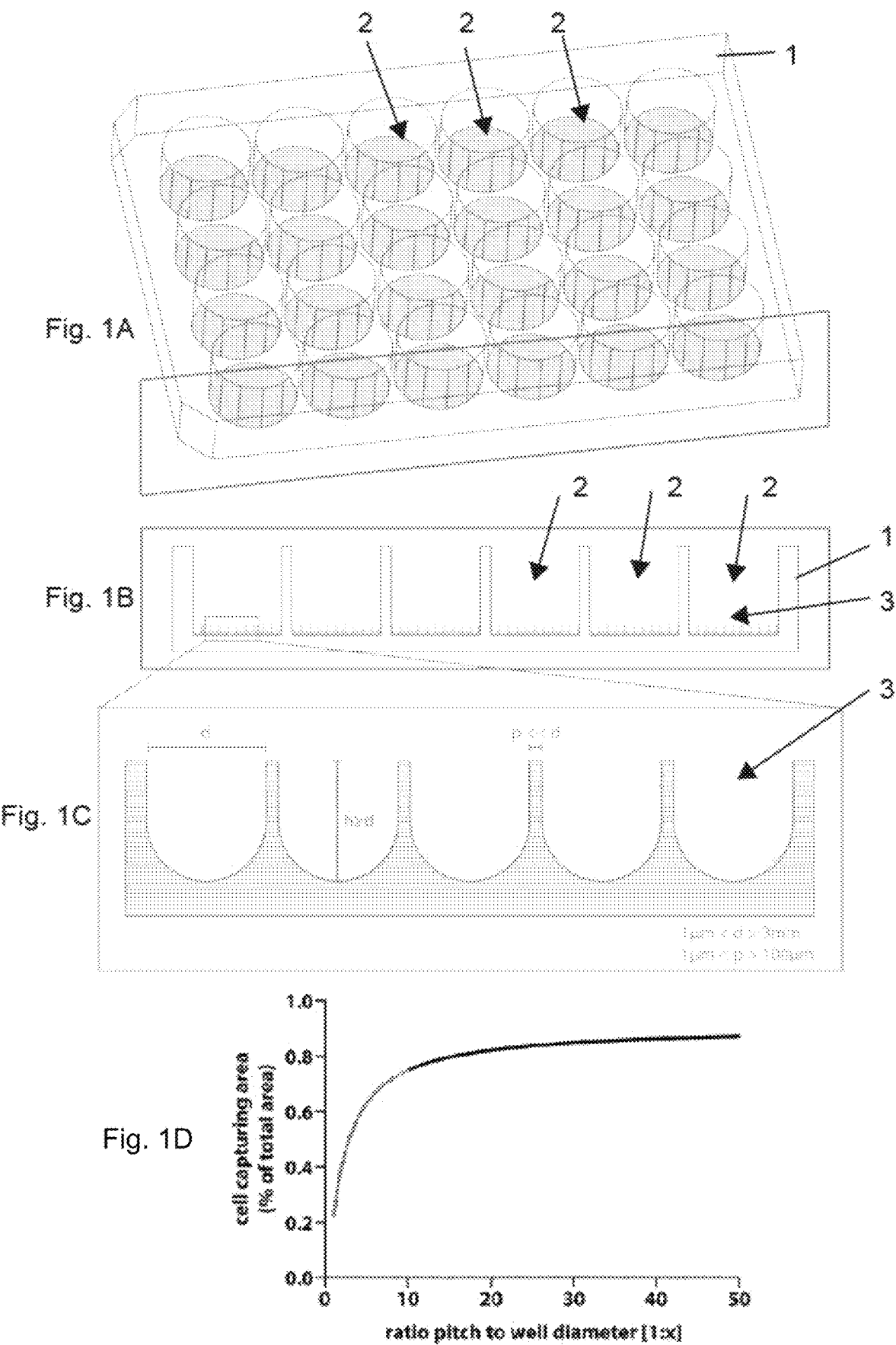
FIGS. 1A to 1D illustrates the principles of the present invention.

In one embodiment, the invention concerns a device for aggregating cells, said device comprising at least one cavity wherein said cavity comprises a plurality of microwells for receiving at least one cell, wherein each said well comprises a vertical sidewall and a curved bottom.

Preferably, the device comprises a plurality of cavities, each said cavity comprising a plurality of microwells.

In one embodiment, the diameter (d), the height (H) and the interwell distance (pitch, p) of the microwells are uncoupled and can be varied independently of each other.

In one embodiment, the microwells have an opening diameter of 1 μm to 3 mm.

In one embodiment, the microwells have heights (h) of 1 μm to 3 mm.

In one embodiment, the microwells have cavities of different sizes or shapes.

In one embodiment, the spacing (pitch size) between the microwells is minimal such that cells falling within the area of the well will fall into a microwell and participate in aggregate formation.

In one embodiment, the spacing between the microwells is in the range of 1 μm to 100 μm.

In one embodiment, the device comprises a microfluidic network with channels.

In one embodiment, the network of channels is beneath the plane of the microwells.

In one embodiment, the network of channels is aligned with the microwells.

In one embodiment, the distance between the network of channels and the bottom of the microwells is less than 500 μm.

In one embodiment, said microwells are made in a hydrogel layer.

In one embodiment, the hydrogel layer is based synthetic hydrophilic polymers, or naturally derived components or hybrids of synthetic polymers and naturally derived components.

In one embodiment, the synthetic hydrophilic polymer is selected from the group comprising poly(ethylene glycol), polyaliphatic polyurethanes, polyether polyurethanes, polyester polyurethanes, polyethylene copolymers, polyamides, polyvinyl alcohols, poly(ethylene oxide), polypropylene oxide, polyethylene glycol, polypropylene glycol, polytetramethylene oxide, polyvinyl pyrrolidone, polyacrylamide, poly(hydroxyl ethyl acrylate), poly(hydroxyethyl methacrylate), or mixtures thereof.

In one embodiment, the hydrogel is prepared by mixing and cross-linking of at least two precursor components using a chemical reaction, wherein the first precursor component comprises n nucleophilic groups and the second precursor component comprises m electrophilic groups, wherein n and m are at least two and the sum n+m is at least five, and wherein the crosslinking is preferably conducted between a multi-arm-PEG macromer, preferably a four-arm-PEG macromere, end-functionalized with nucleophilic, preferably thiol-groups, with a multi-arm-PEG macromere, preferably an eight-arm-PEG macromere, end-functionalized with electrophilic, preferably vinylsulfone-groups at appropriate concentrations and conditions such as to allow for the cross-linked hydrogel layer to exhibit a shear modulus between 0.1 and 100 kPa.

In one embodiment, the hydrogel comprises an excess of free functional groups, preferably nucleophilic groups, more preferably chosen from the group comprising amines and thiols, and—in addition or alternatively—electrophilic groups, preferably chosen from the group comprising acrylates, methacrylates, acyl-amides, methacrylamides, acylonitiriles, quinones, vinyl-sulfones, maleimides and their derivates.

In one embodiment, the microwells may be functionalized with one or more types of bio-molecules.

In one embodiment, the biomolecules are proteins, oligopeptides, oligonucleotides, or sugars.

In one embodiment, the proteins or peptides are ECM-derived or ECM-mimetic and attached to the nucleophilic or electrophilic groups, preferably the thiol groups of the PEG-based layer, using a heterobifunctional linker, wherein one functional group of the linker is reactive to the functional groups attached to termini of the polymer chains and the other functional group of the linker selected from the group comprising succinimidyl active ester such as N-hydroxysuccinimide (NHS), succinimidyl alpha-methylbutanoate, succinimidyl propionate, aldehyde, thiol, thiol-selective group comprising acrylate, maleimide or vinylsulfone, pyridylthioesters and pyridyldisulfide, is capable of nonspecifically tethering to the biomolecule of interest via its amine groups.

In one embodiment, the biomolecules are tagged such as to be tethered to the hydrogel surface by affinity.

In one embodiment, the tagged biomolecules have tags to enable binding to targets chosen from the group comprising ProteinA, ProteinG, ProteinA/G, Streptavidin, NeutrAvidin, NTA, antibodies, S-fragment of RNaseA, calmodulin, cellulose, chitin, glutathione, amylose, or functionalized oligopeptides and oligonucleotides having nucleophilic or electrophilic functional groups that can react with the functional groups on the hydrogel network.

In one embodiment, the naturally derived components are selected from the group comprising polysaccharides, gelatinous proteins, and ECM components such as agarose, alginate, chitosan, dextran, gelatin, laminins, collagens, hyaluronan, fibrin or mixtures thereof or are selected from the group of complex tissue derived matrices comprising Matrigel, Myogel and Cartigel.

According to the present invention, novel culture platforms made of high-density micrometer-scale U-bottom shaped microwells for the reproducible formation of cellular aggregates and their long-term culture is described. Such platforms are of high interest as these aggregates were shown to form self-organized structures displaying enhanced cellular function and, thus, stronger relevance in contrast with conventional culture systems.

Even though other cell aggregation platforms, such as the above-described AggreWells' (Ungrin et al. 2008) and others (Giselbrecht et al. 2006, Chen et al. 2008, Choi et al. 2010, Liu et al. 2014) have been described over the past decade, none of them were able to fabricate microstructures giving a satisfactory cell aggregation. Indeed, spherical micrometer-scale pattern fabrication is a main bottleneck in microtechnologies, as most of the standard processes form structures with edges.

A recent study has demonstrated the fabrication of quasi-spherical microwells through the use of ice lithography and subsequent PDMS replication (Liu et al. 2014). While simple and easily produced with commonly available tools, this technique is still limited by the interdependence of height, diameter and pitch size of the formed microwells. Further, the scalability of the platform is questionable, as demonstrated by the low number of spheroids per array (below 25).

In contrast, by taking advantage of solvent evaporation from dilute polymer solution, such as the epoxy-based negative photoresist SU-8, an evaporation meniscus is formed at the interface of the condensing liquid on the rigid surface, granting the ability to form densely packed spherical microstructures with high geometrical reproducibility.

The main strength of the present invention is the decoupling of the microwell diameter, height and the inter-well distance that grants a total freedom in array geometry. The ability to vary these three parameters independently, an impossibility in the aforementioned already existing prior art platforms, is needed to develop biological application-based platforms rather than platforms in search for applications.

Also, the proposed U-bottom shaped microwell arrays are preferably formed with soft and highly hydrated substrates such as hydrogels rather than elastomers, such as PDMS, to mimic as close as possible the physiological environment of cells.

It was demonstrated that single cell survival on the proposed substrate was significantly higher than PDMS-based platforms (such as disclosed in the KR prior art application cited above) and that cell aggregate growth was catalyzed on the proposed substrate.

On the other hand, these results corroborate with the recent demonstrations of hydrogel potency to support cell culture compared with non-hydrated substrates.

On the other hand, three-dimensional cell culture systems have appeared to be a major answer to the lack of relevance of two-dimensional systems.

With the present hydrogel-based microwell array platform, it was demonstrated that one could link the ability to aggregate cells in a high-throughput fashion and the potential to provide these cells a three-dimensional environment by encapsulating them in an upper layer of hydrogel. In addition, as the platform is made of hydrogel, one could show the possibility to integrate microfluidic networks into the platform.

And, as an additional advantage of the use of hydrogel, one could demonstrate the possibility to chemically cross-link biofunctional ligand onto the microwells surface enabling the assessment of the influence of tethered cues on the cultured aggregates. The integration of three-dimensional culture, microfluidic networks and microwell patterning and biofunctionalization into the same platform opens a totally new physico-chemical and spatio-temporal space for high-resolution screenings of 3D microtissues.

Finally, one shows that the platform could be used with any cell type, and more specifically, with non spheroid-forming cell types such as MDA-MB231, human breast cancer cells, that formed aggregates after two to three days and kept tightly aggregated for at least five days.

The present invention presents the unique opportunity to enable "controllable" cell co-cultures. Co-cultures are possible by either initially seeding multiple cell types simultaneously or through the addition of other cell types to an ongoing spheroid culture. Additionally, more than two cell types can be added at any given time during the culture to allow for the systematic study of self-organization, migration and cell redistribution.

The presented technology is a highly versatile and innovative multidimensional screening platform for high-resolution screenings in space and in time. The present approach consists in biological application specific-based platform development unlike most of the aforementioned platforms. It is believed that these kind of fully integrated technologies will support fundamental biology advances as well as strongly catalyze translational research to clinics.

FIGS. 1A to 1D illustrate the principle of the present invention.

According to this principle, a plate 1 is provided with a series of wells 2. Typical sizes of said commercially available wells 2 are about 6.4-34.8 mm in diameter and 1.76 cm in depth holding total liquid volumes of 0.36-16.8 mL corresponding to working volumes of 0.1-0.2 mL to 1.9-2.9 mL. This is of course an example and other plates 1 may be used with other sizes, either commercially available plates or specifically made plates.

FIG. 1B shows a side cut view of the plate 1 of FIG. 1A with its wells 2. One sees in this FIG. 1B a set of microwells 3 which are placed at the bottom of each well 2 which forms one feature of the present invention.

Said microwells 3 are illustrated in more detail in FIG. 1C which is an enlarged view taken from a well 2 of FIG. 1B.

Accordingly, the present invention in an embodiment proposes to provide a set of microwells 3 in a set of larger wells 2 of a plate 1.

Figure 2:
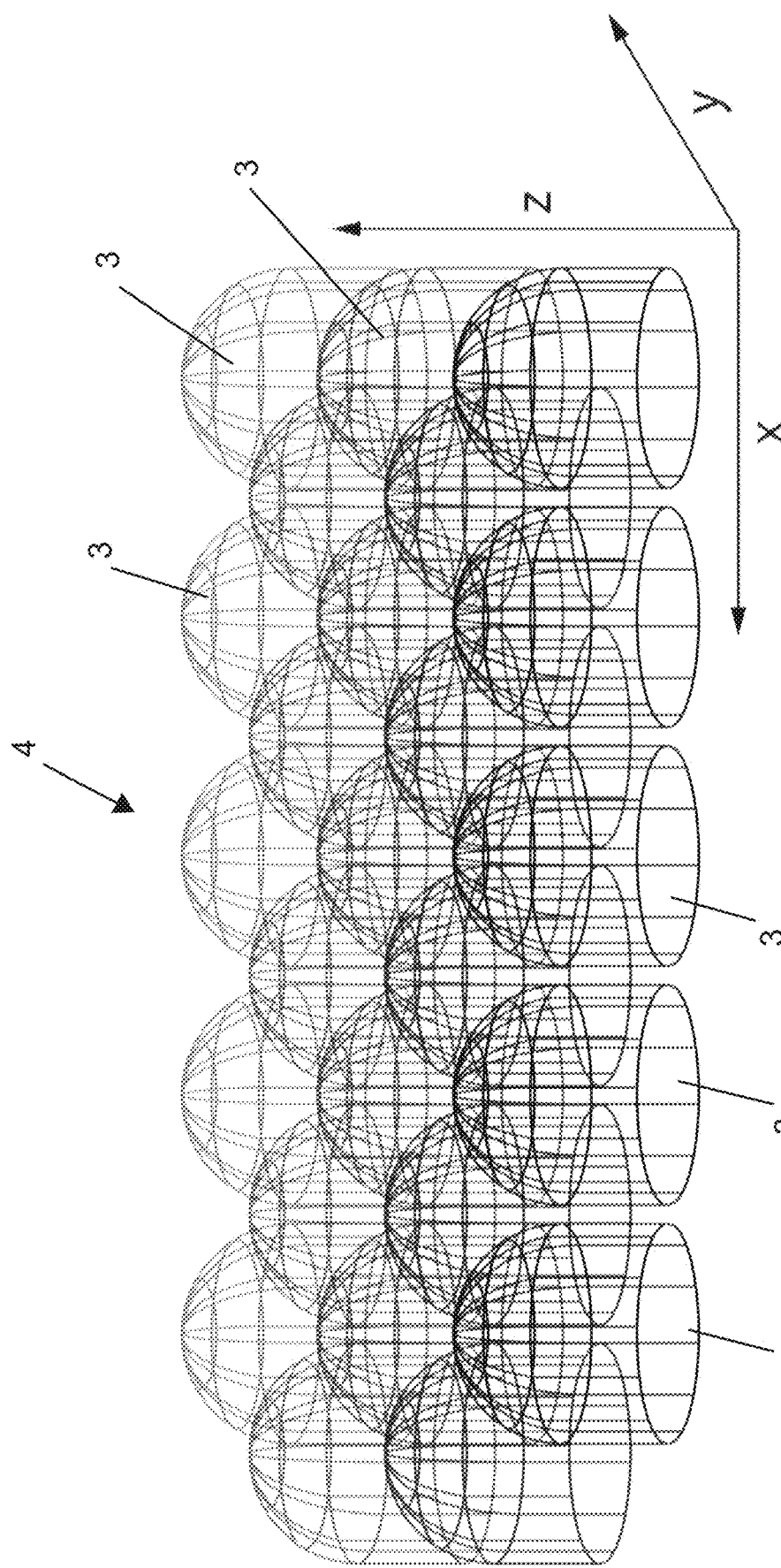
FIG. 2 illustrates a microwell array three-dimensional geometry (inverted) according to the present invention.

FIG. 2 shows a microwell 3 array 4 with a three-dimensional geometry (inverted). For visualization purposes, the three dimensional geometry of the microwell array 4 is shown inverted. This illustrates the generic structure of U-bottom microwells 3 in a perspective illustration of a negative PDMS stamp (for example) used to cast a U-bottom microwells array.

Figure 3:
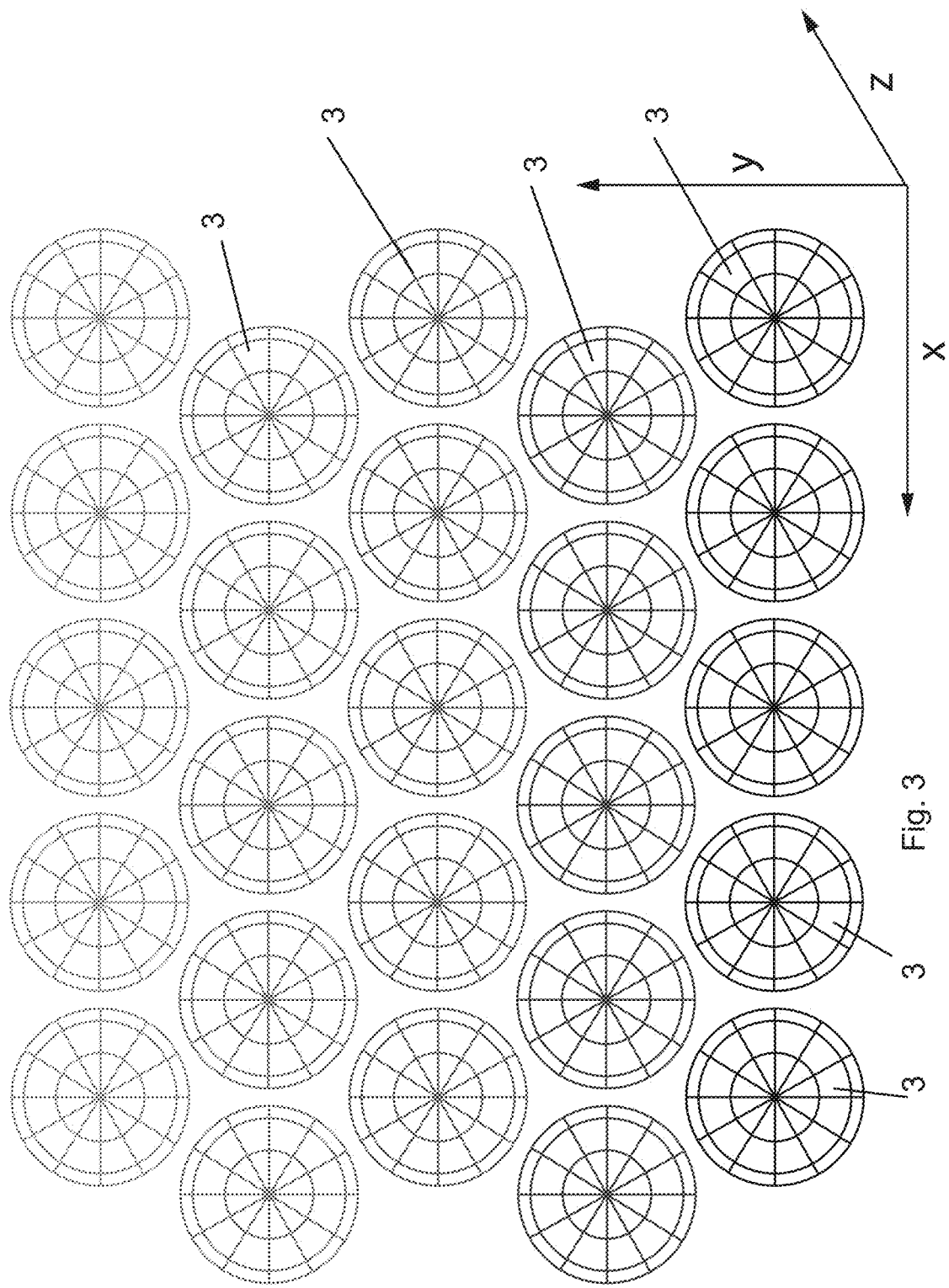
FIG. 3 illustrates a microwell array top view geometry.

FIG. 3 illustrates an example of a microwell array 4 in top view geometry. The theoretical top view of these arrays 4 is shown here. The microwells 3 have been organized in order to maximize the density of wells for a given area of the array 4. Also, this organization of microwells 3 allows to minimize the inter-well distance, thus, preventing cells to grow in-between microwells 3.

The distances d, h and p, which are defined in FIG. 1C, can be chosen independently with the fabrication techniques that are described in the present application. As examples, the size of d and h can range from 1µ to 3000 µm (3 mm); the size range of p can be freely chosen. For optimal use of the device, h should be always larger than or equal to d and p should be as small as possible, much smaller than d ($p \ll d$) and typically in the range of 1 µm-100 µm. If needed, p larger than 100 µm can be realized without restrictions.

FIG. 1D illustrates the percentage of cell capturing area (area covered by microwells) as a function of the pitch size to well diameter ratio. At a ratio of 10:1, the microwells already cover 74.95% of the total area. This percentage cannot be significantly increased by further decreasing the pitch size.

Figure 4:
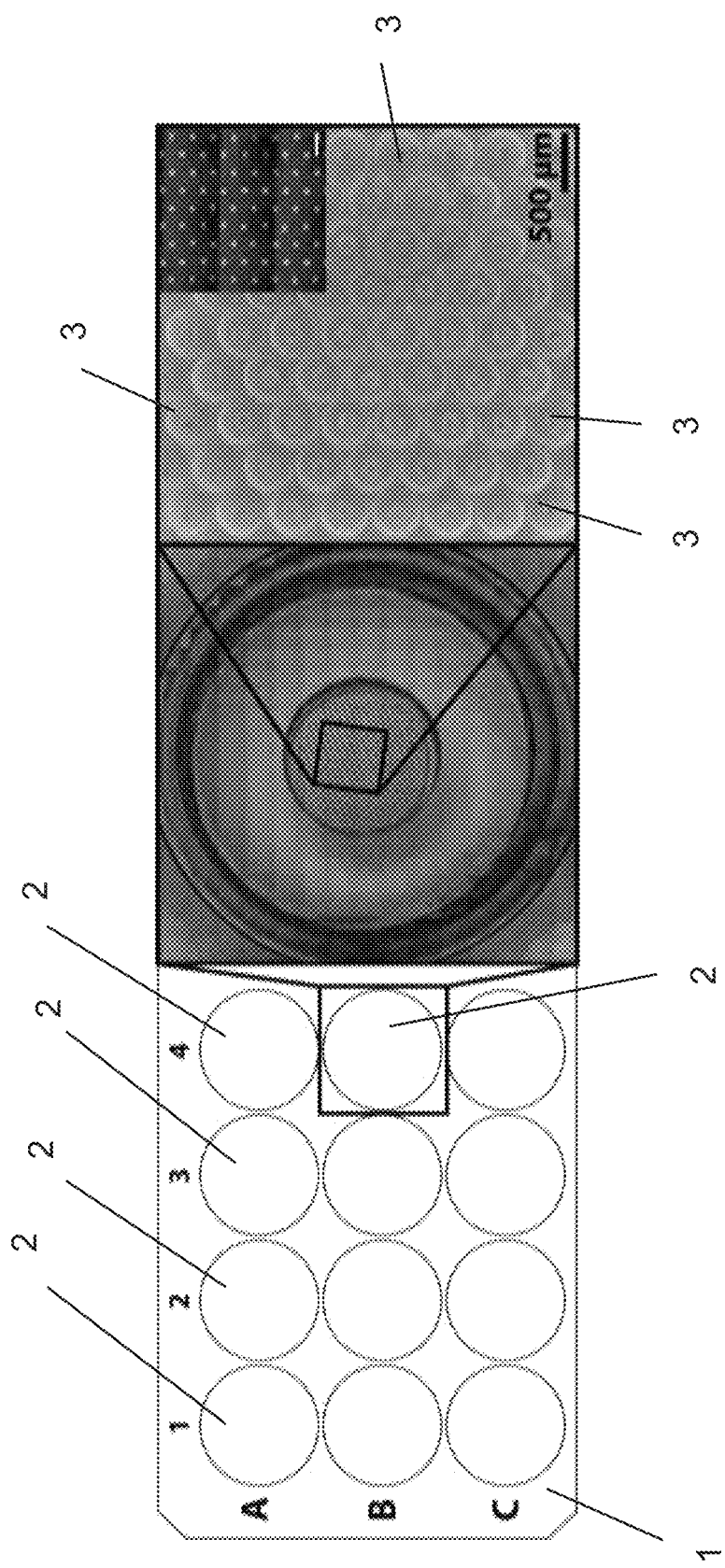
FIG. 4 illustrates an overall view of an U-bottom microwell array.

FIG. 4 illustrates an overall view of a U-bottom microwell 3 array. An array with a bottom diameter of 8 mm is cast in a well 2 of a 12-well plate 1 (see FIG. 1A). Brightfield and fluorescent representation (small insert, left) of an area of the array 4 with 72 microwells 3 containing clusters of Oct4:: GFP ESCs are shown. The size of the aggregate is monodisperse and the pluripotency marker Oct4 is displayed in each cell cluster. This aggregate homogeneity illustrates the strong reproducibility of the U-bottom microwell 3 platform.

The following table 1 gives examples of well plates 1 (see FIG. 1A) with different numbers of wells 2 per plate (6, 12, 24, 48 and 96), the well bottom area and the microwells 3 diameter depending on the number of microwells 3 per well 2.

TABLE 1

| | Wellplate 1 | | | | |
|---|---|---|---|---|---|
| | 6-well | 12-well | 24-well | 48-well | 96-well |
| | bottom diameter (mm) | | | | |
| microwell 3 | 34.8 | 22.1 | 15.6 | 11 | 6.4 |
| | bottom area (cm2) | | | | |
| diameter (µm) | 9.5 | 3.8 | 1.9 | 0.95 | 0.32 |
| 50 | 135591 | 54683 | 27247 | 13547 | 4586 |
| 100 | 56035 | 22598 | 11260 | 5598 | 1895 |
| 200 | 19067 | 7689 | 3831 | 1905 | 644 |
| 300 | 9500 | 3831 | 1909 | 949 | 321 |
| 400 | 5672 | 2287 | 1139 | 566 | 191 |
| 500 | 3766 | 1518 | 756 | 376 | 127 |
| 600 | 2681 | 1081 | 538 | 267 | 90 |
| 700 | 2005 | 808 | 403 | 200 | 67 |
| 800 | 1556 | 627 | 312 | 155 | 52 |
| 900 | 1242 | 501 | 249 | 124 | 42 |
| 1000 | 1015 | 409 | 204 | 101 | 34 |
| 1250 | 659 | 266 | 132 | 65 | 22 |
| 1500 | 463 | 186 | 93 | 46 | 15 |
| 1750 | 342 | 138 | 68 | 34 | 11 |
| 2000 | 263 | 106 | 53 | 26 | 8 |

One of the advantages of the present invention is that it allows an easy refilling of the medium in the microwells 3. Indeed, rather than refill each of said microwells 3 individually, which is, in addition, impossible below a given microwell size. With the present invention, it is possible to act at the level of the wells 2 which are larger than the microwells 3 and thus easier to refill.

Figure 5:
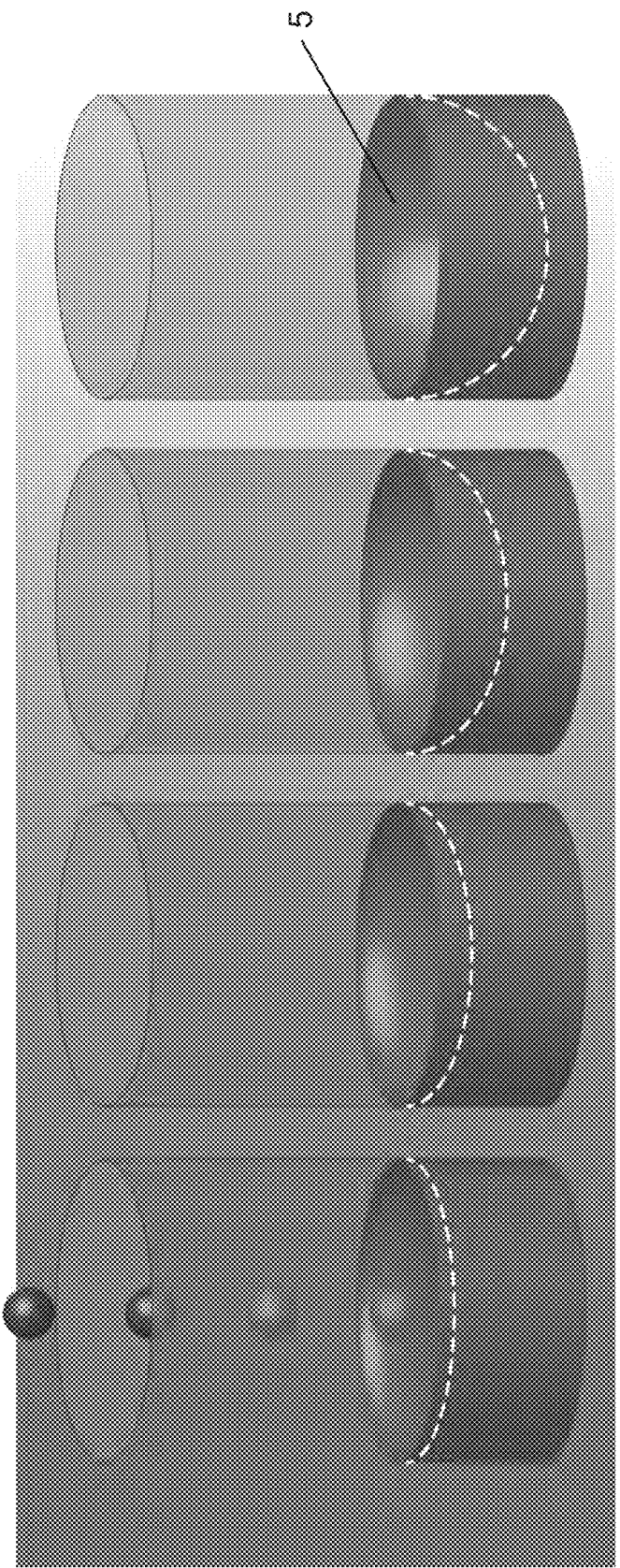
FIG. 5 illustrates a conceptual description of the U-bottom well fabrication process.

FIG. 5 illustrates a conceptual representation of a U-bottom microwell 3 fabrication process according to the present invention. U-bottom microwells 3 are formed through defined volume deposition of dilute liquid materials, for example polymers, such as the epoxy-based photoresist SU-8, to allow spherical bottom shape formation through solvent evaporation. During solvent evaporation, the deposited material condenses and wets the microwell 3 wall to form an inverted half spherical bottom shape 5 at the bottom of the wells through surface tension forces. After solidification of the deposited material, the structures can be used for replica moulding to fabricate the microwell 3 arrays 4.

Figures 6A, 6B, 6C:
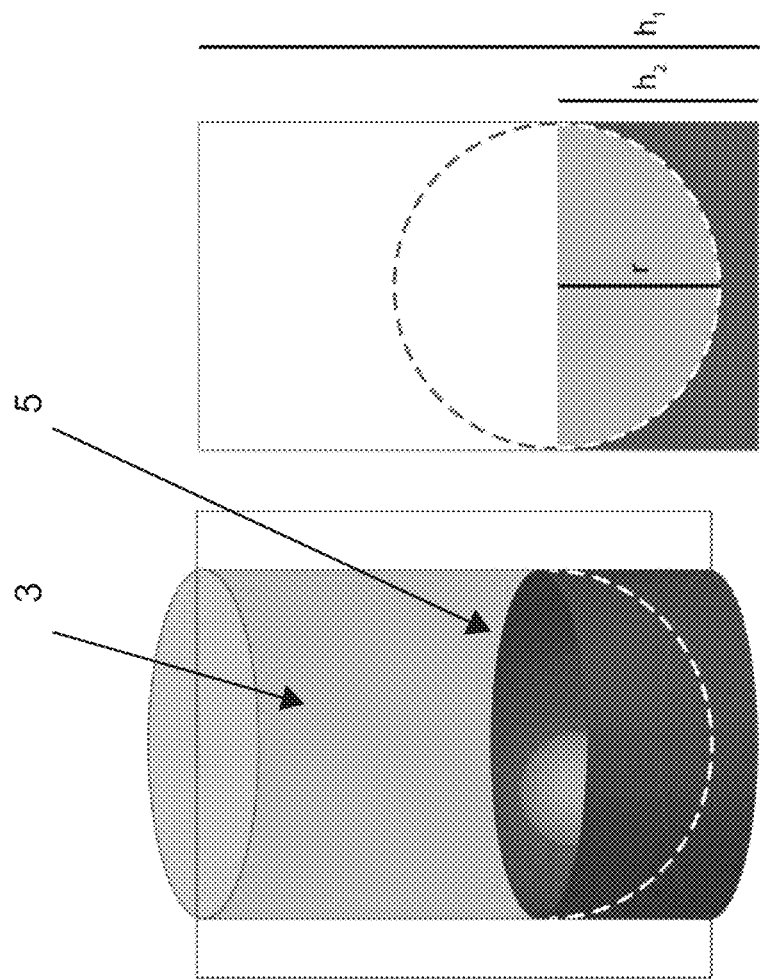
FIGS. 6A to 6C illustrate a theoretical and actual view of the geometry of a U-bottom microwell.

FIG. 6A illustrates a theoretical description of the final geometry of a microwell post-evaporation, as discussed above in relation to FIG. 5. A perspective illustration of a single Si well 3 with inverted SU-8 cap 5 at the bottom of the well is shown including a cross-section along the center. r depicts the radius of the inverted cap, that equals the radius of the pre-etched well. h1 relates to the depth of the well equal to the depth pre-etched in Si. h2 relates to the total height of printed SU-8 before solvent evaporation, approximating the radius of the pre-etched well (FIG. 6B). an example of a microwell 3 with SU-8 deposition to form a U-shaped well bottom (bottom left) or without (bottom right) replica-molded into PEG hydrogel is given in the image of FIG. 6C.

Figure 7:
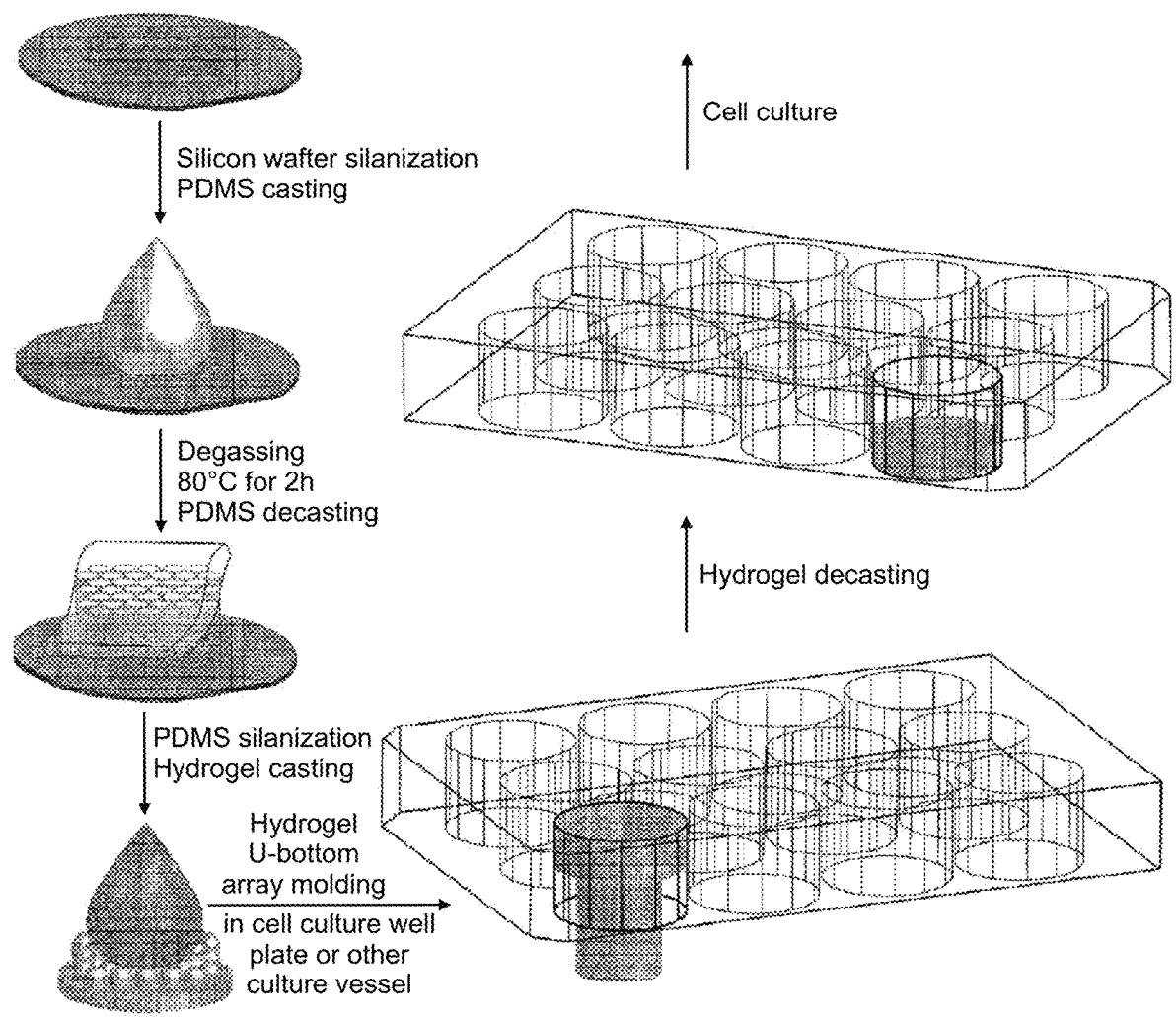
FIG. 7 illustrates a conceptual description of hydrogel casting.
Figure 9A:
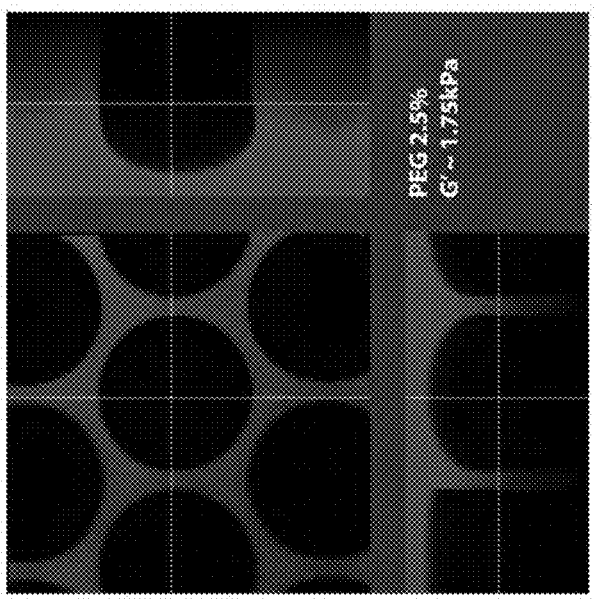
FIGS. 9A to 9D illustrate U-shaped microwells reproduced in materials with different stiffness.
Figure 9B:
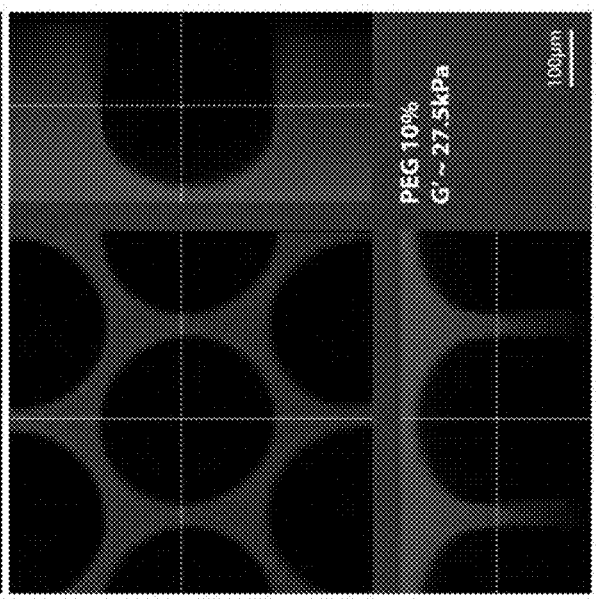
Figure 9C:
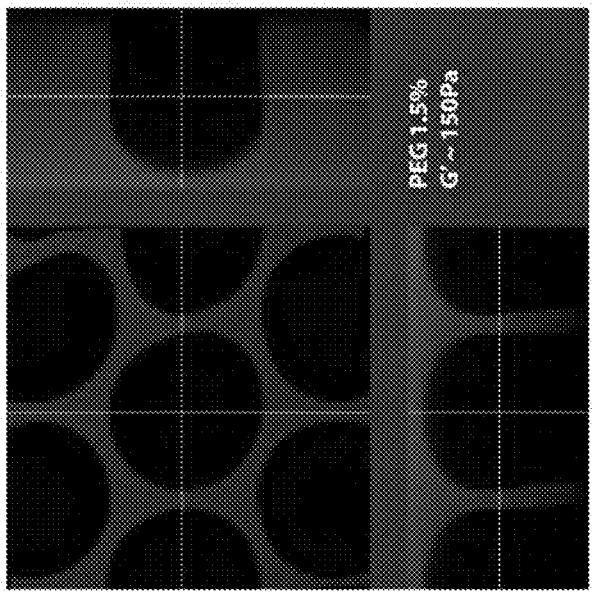
Figure 9D:
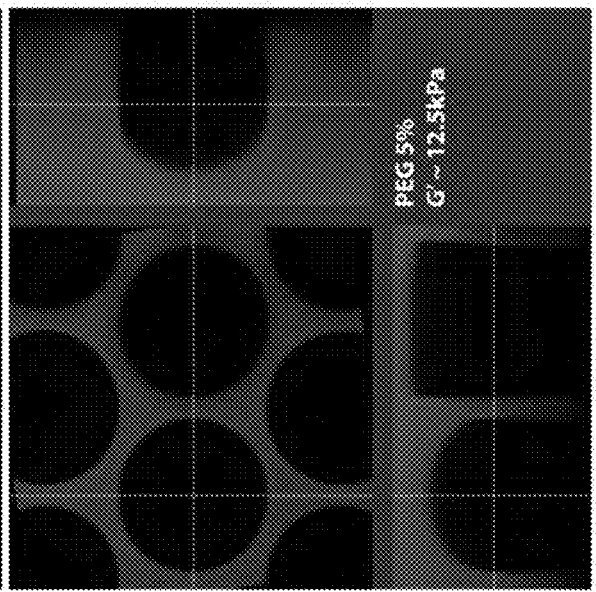

FIG. 7 illustrates an example of a conceptual description of PDMS & hydrogel casting of a plate 1 according to the present invention. After silanization of the template silicon stamp to render the surface hydrophobic, the U-bottom structures are replica-molded into PDMS. The formed PDMS U-bottom microwell negative is then used to cast any desired material onto coverslips or directly at the bottom of wells 2 of tissue culture plates 1. Coverslips, where employed, may be fixed in any suitable manner in the wells 2, for example through biocompatible adhesive thin films, such as thin layers of PEG hydrogel.

FIGS. 8A-8D illustrates examples of different U-shaped microwell sizes. Using PEG hydrogel (G'~12.5 kPa), different combinations of the varying parameters, (d, distance, h, height and p, pitch were achieved. Confocal images (orthogonal views) of microwells 3 of 100 µm, 250 µm, 400 µm and 1.25 mm diameter are represented (A-D). The exact design of these three different samples is the following:

FIG. 8A: the microwell 3 has a diameter of 100 µm, a height of 200 µm and an interwell distance of 40 µm.

FIG. 8B: the microwell 3 has a diameter of 250 µm, a height of 400 µm and an interwell distance of 40 µm.

FIG. 8C: the microwell 3 has a diameter of 400 µm, a height of 400 µm and an interwell distance of 40 µm.

FIG. 8D: the microwell 3 has a diameter of 1.25 mm, a height of 1 mm and an interwell distance of 40 µm.

This shows the strong versatility of the platform of microwells according to the present invention.

FIG. 9A to 9D illustrates U-bottom microwells in different stiffness. Using PEG hydrogels with varying polymer content (w/v, 1.25%, 2.5%, 5%, 10%, as indicated in the drawings) different absolute stiffness were demonstrated to be moldable as U-bottom microwell arrays. The U-bottom microwell structures of the present invention were easily imprinted in hydrogels having a stiffness of 150 Pa (G'), FIG. 9A, to approx., 30 kPa (G'), FIG. 9D. This wide coverage is crucial to address biological questions relating to cell aggregate interactions with substrates of varying rigidity.

Figure 10:
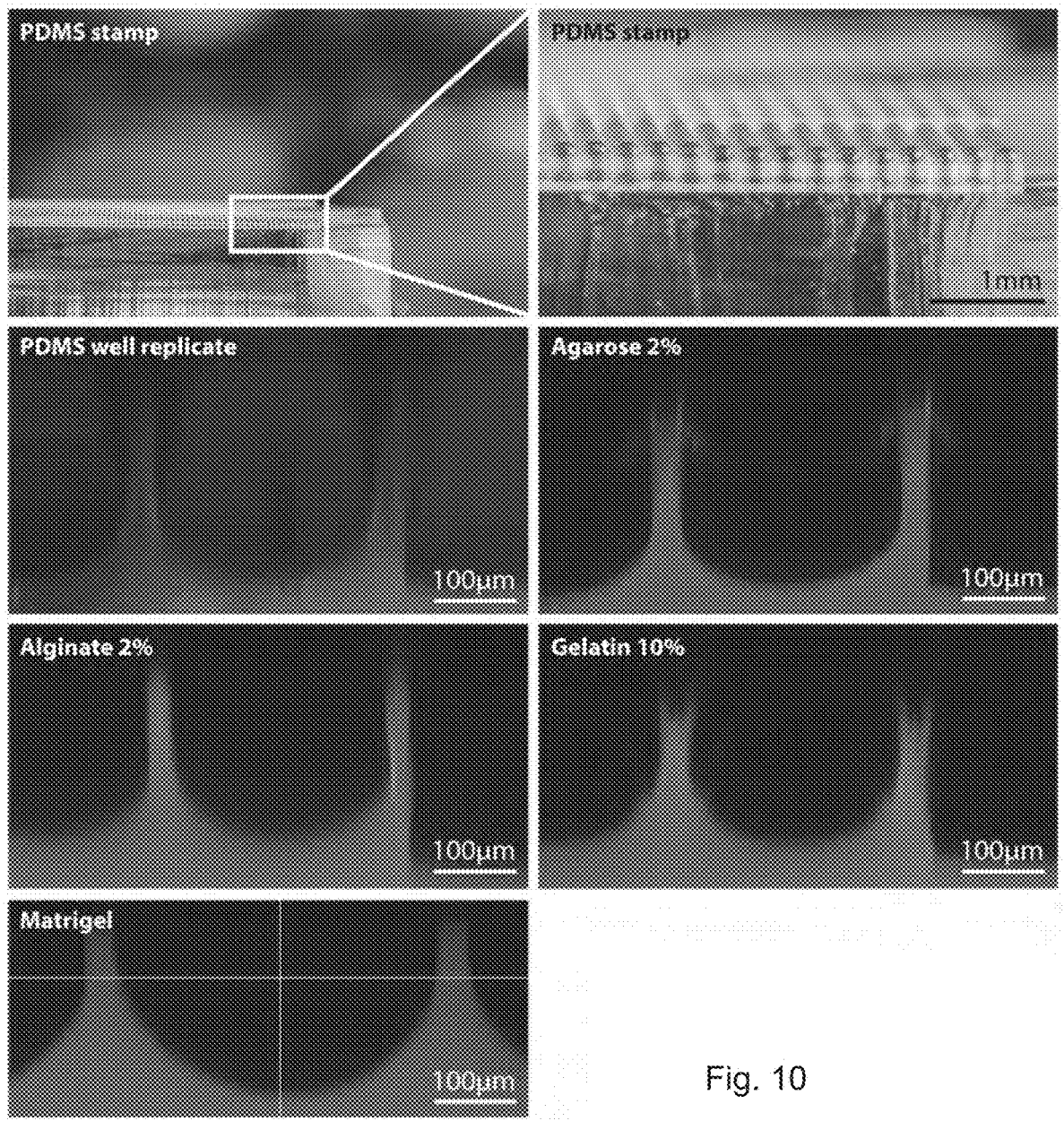
FIG. 10 illustrates examples of U-shaped microwells produced in a variety of materials as indicated.

FIG. 10 illustrates the variety of materials that may be used as indicated in the drawings. From the PDMS negative mold, diverse materials were imprinted with the above-described pattern. PDMS can be replica molded to give rise to U-bottom microwell arrays in PDMS. Preferably the U-bottom microwell arrays are reproduced in soft biocompatible polymers: standard synthetic hydrogels such as polyethylene glycol (PEG) were demonstrated to be moldable as well as natural hydrogels, such as agarose, alginate, gelatin, matrigel and collagens. Of course, other equivalent materials may be used.

Figure 11:
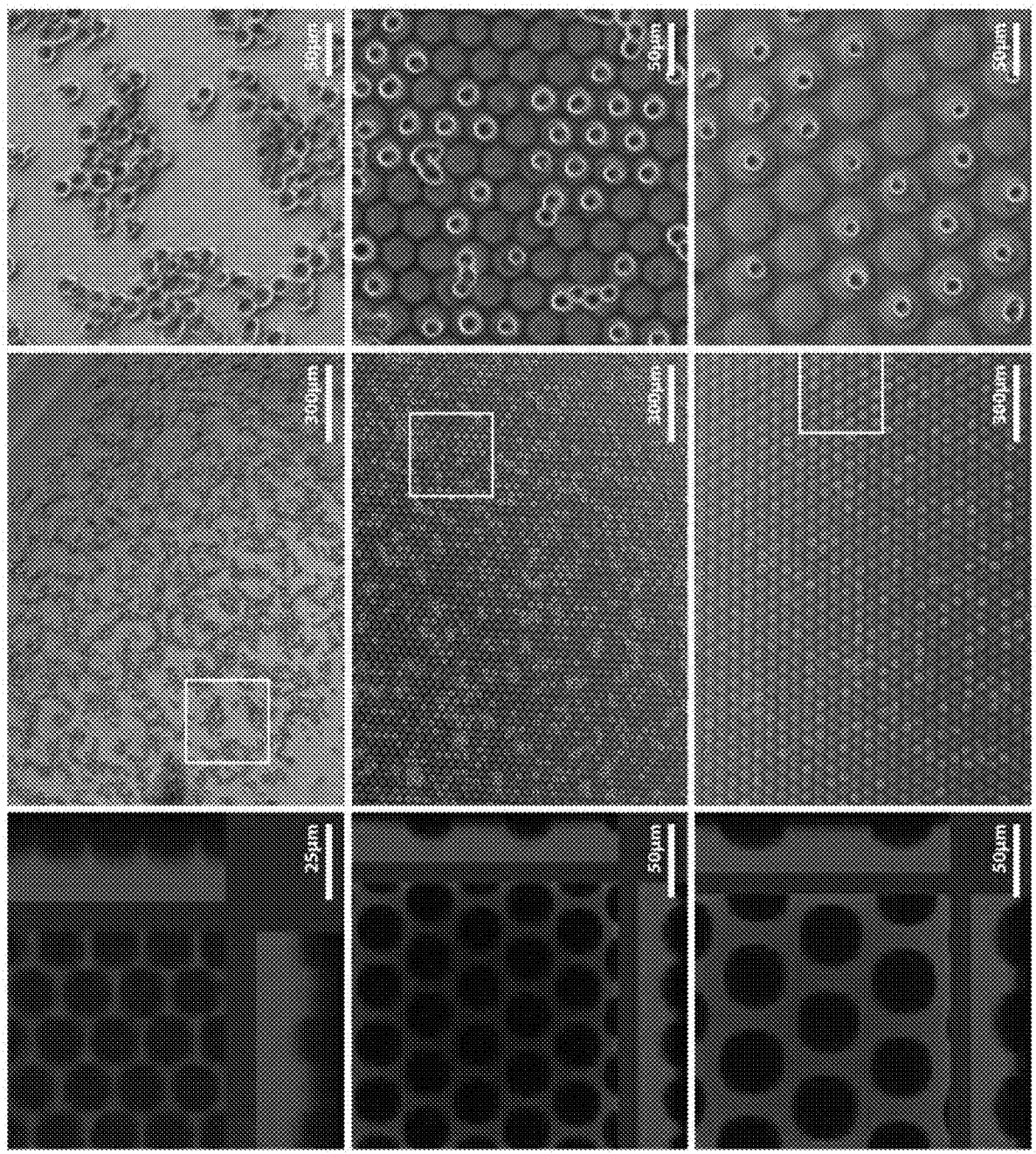
FIG. 11 illustrates examples of small sizes microwells.

FIG. 11 illustrates an embodiment of small sizes wells. Microwells 3 of sizes comprised between 10 and 50 µm wells were moulded in 12.5 kPa PEG hydrogel to create a single cell culture platform. Single cells were successfully seeded in separate well.

Figure 12:
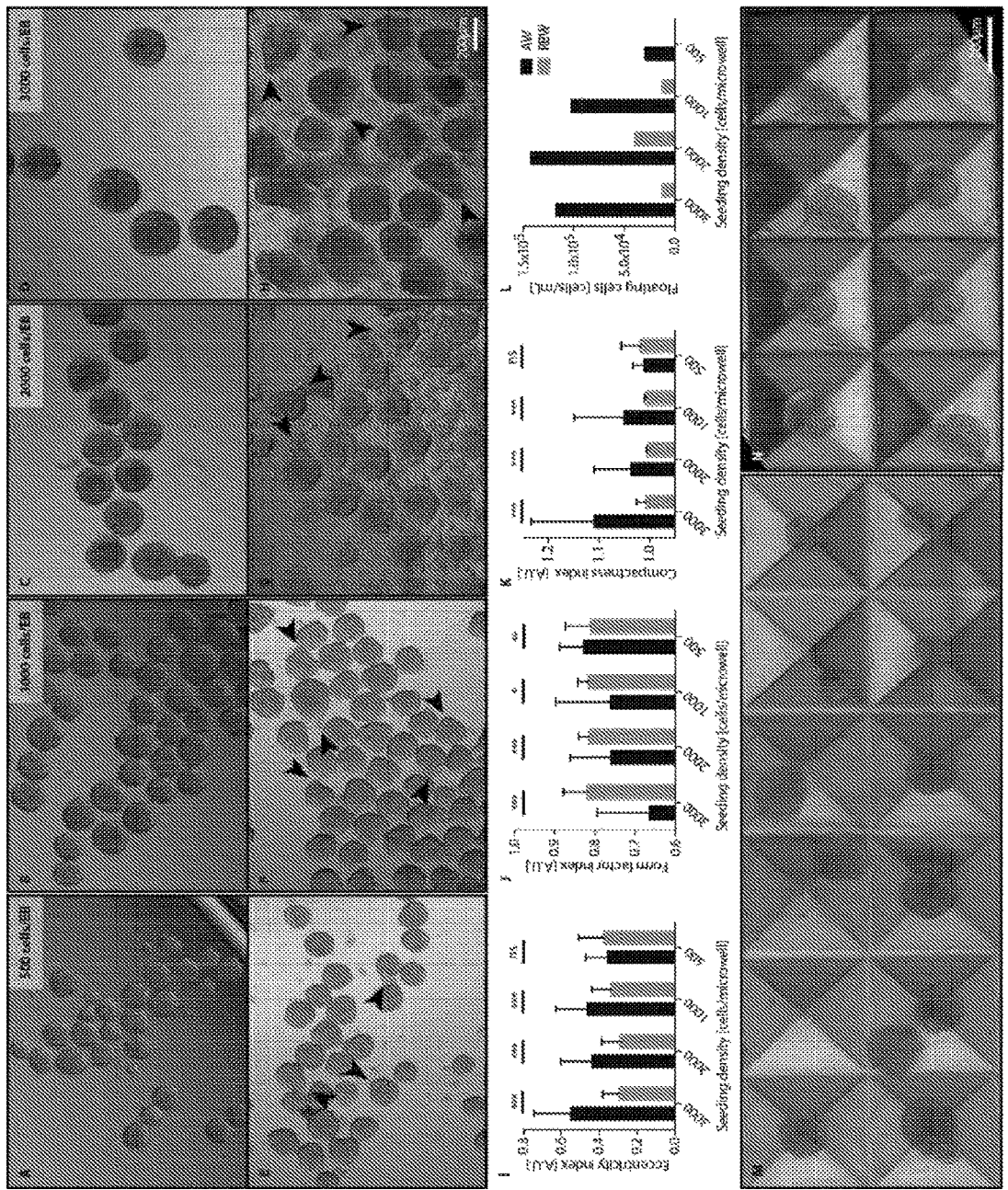
FIGS. 12A-N illustrate limitations of the standard AggreWell™ platform.

FIG. 12 (A) to (N) shows the limitations of the standard AggreWell™ platform. Brightfield representations of harvested Oct4::GFP ESCs aggregates (i.e. 500, 1000, 2000 and 3000 cells per microwell) after 24 h of culture in 400 µm diameter U-bottom microwells (A-3) as well as 400 µm dimensioned Aggrewells™ (E-H). Several limitations of the AggreWell™ platform were observed. As already suggested, (Shiku et al. 2013) cells aggregating in pyramidal shape microwells adopt a pyramidal shape (top). This can be seen with many different cell-seeding densities, for example 500, 1000, 2000 and 3000 cells per microwells (arrows). However, cells aggregates formed in U-bottom microwells were significantly more round. Indeed, the spheroid eccentricity (I), form factor (J) and compactness (K) were found to be significantly different between the U-bottom microwells and the Aggrewells™ for most of the cell densities. This lack of compactness was confirmed by assessing the number of floating cells after harvesting between the two platforms (L) and we found that, after harvesting, more single cells were floating in the supernatant of Aggrewells™ conditions compared to those of the U-bottom microwells of the present invention. Finally, using time-lapse imaging, cell aggregates such as Oct4:GFP ESCs (M) and NIH3T3 fibroblasts (N) aggregates, seeded onto AggreWell™ surface (PDMS surface) were observed to crawl along the microwells walls. These observations demonstrate the need for novel culture platforms such as the present invention that use more inert culture substrates and culture substrates that show greater biocompatibility than PDMS.

Figure 13:
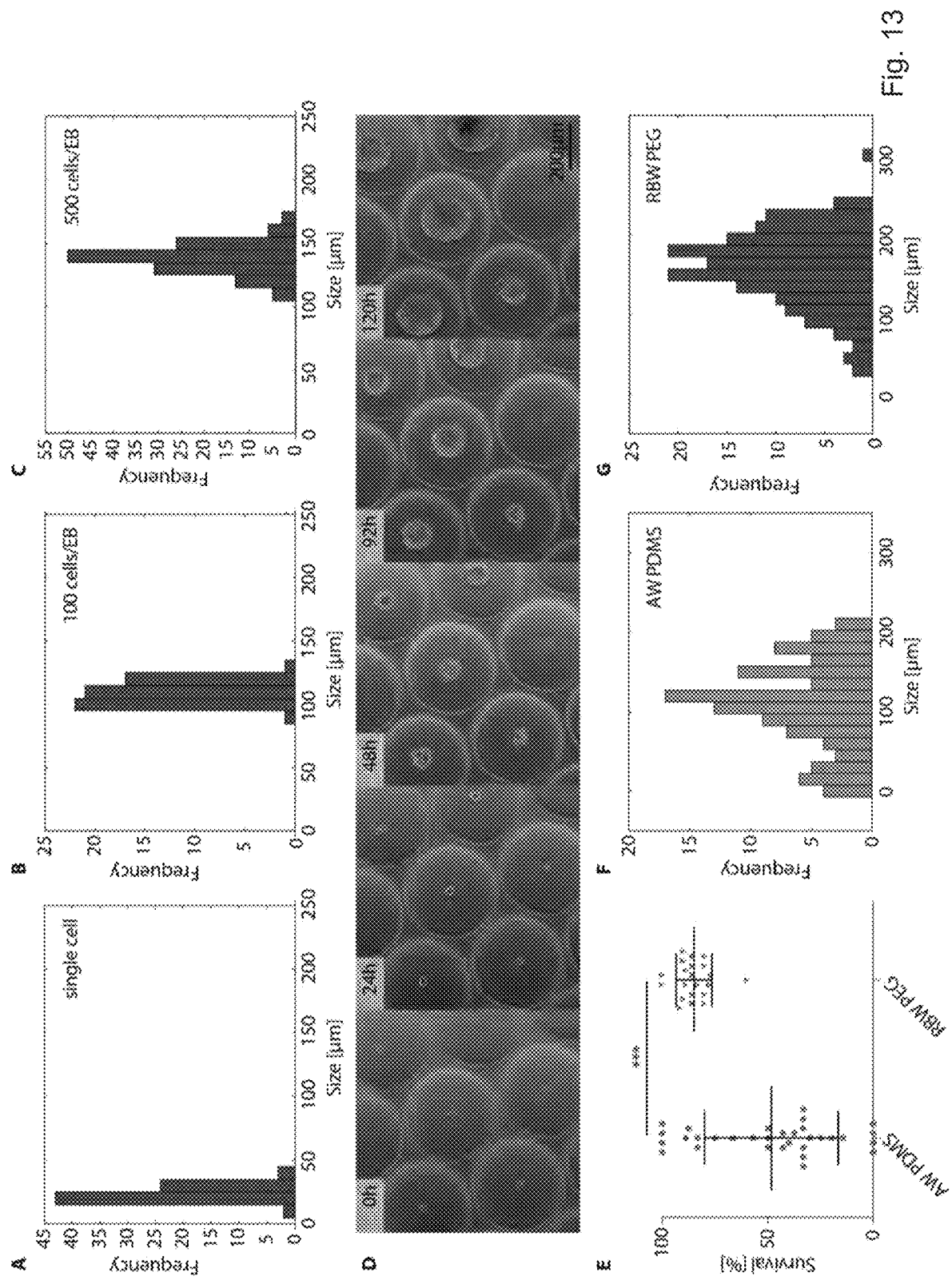
FIGS. 13A-G illustrate an example of varying cell density.

FIG. 13 (A) to (G) illustrates examples of measured varying cell density. Using mouse Oct4::GFP ESCs, three-different cell densities, (A) one cell per microwell, (B) 100 cells per microwell (C) 500 cells per microwells, were seeded into 400 µm diameter and 400 µm height U-bottom microwells. The size distribution of each density was assessed after 24 h. Over this period, the aggregates grew to about 25 µm, 110 µm and 140 µm for one cell per microwell, 100 cells per microwell and 140 cells per microwell, respectively.

(D) Brightfield representations of the growth of single cells over a 5 days period. A difference in growth potential can be observed for different single cells. Therefore, the microwell arrays according to the present invention are a potent tool to assess heterogeneity of stem cell populations at the single cell level, such as their varying clonal expansion potential.

(E) Single embryonic stem cell viability was assessed in U-bottom microwell arrays according to the present invention (RBW PEG) and compared to the standard AggreWell™ arrays (AW PDMS). The arrays according to the present invention supported significantly single cell survival. *** corresponds to $p<0.001$.

(F) the size distribution of clonally expanded colonies from single cells was assessed after 5 days in AggreWell™ and (G) in U-bottom microwell arrays according to the present invention.

Compared to the Aggrewell™ platform aggregates formed and cultured in U-bottom microwells according to the present invention are more homogeneous in size.

Figure 14:
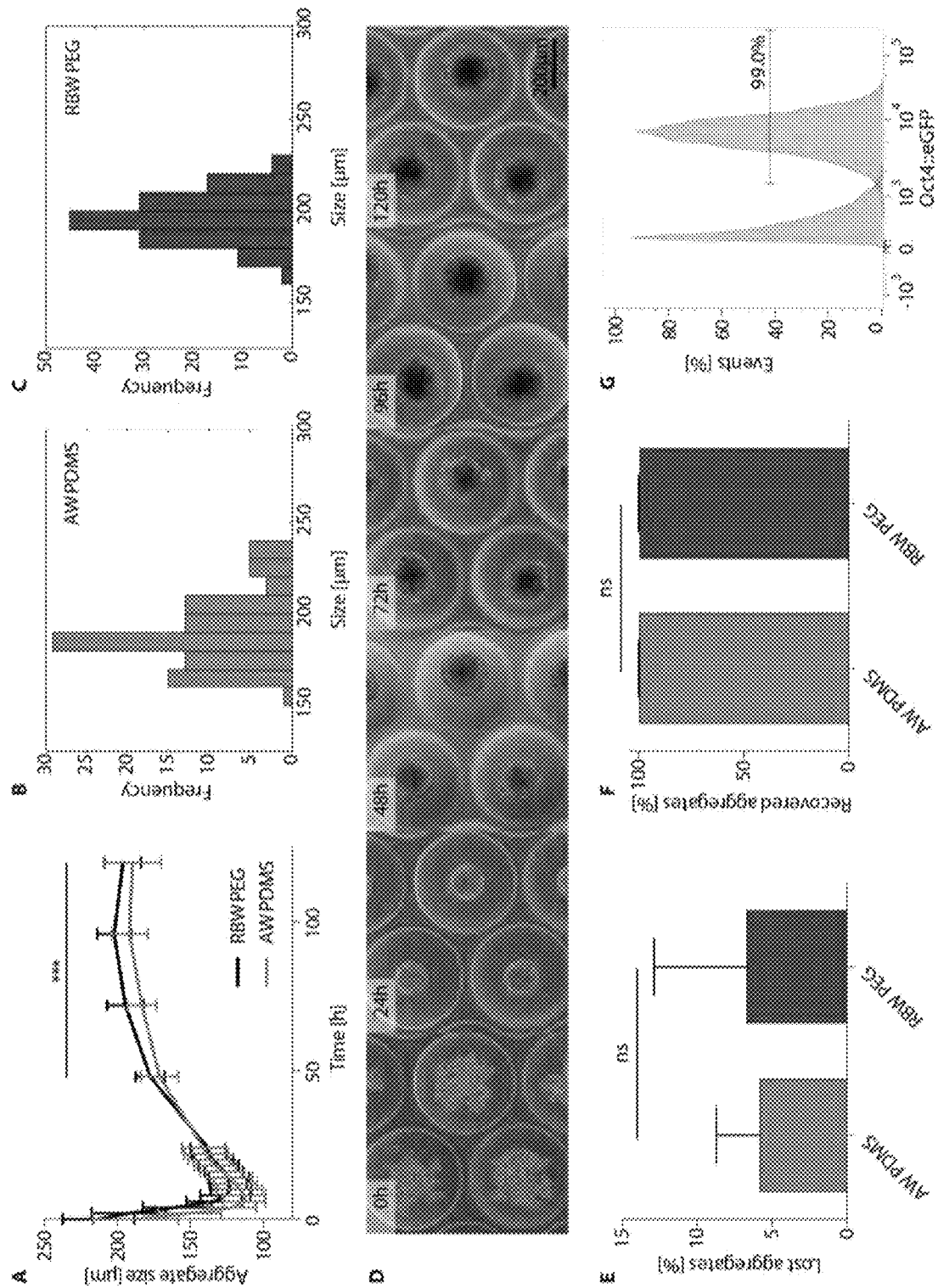
FIGS. 14A-G illustrate an example of aggregate growth, size distribution and pluripotency maintenance.

FIG. 14 (A) to (G) illustrates aggregate growth, size distribution and pluripotency maintenance. Aggregate growth of mouse Oct4::GFP ESCs was assessed for 5 days in the U-bottom microwell platform according to the present invention (RBW PEG) in comparison to the AggreWell™ platform (AW PDMS) (A). After compaction of the cells, the growth of the clusters was significantly improved in the U-bottom microwells according to the present invention in comparison to AggreWells™ (B, C). The size distribution of the aggregates was assessed at day 5. The U-bottom microwell platform according to the present invention (C) shows a higher monodispersity of the aggregates' size compared to AggreWells™ (B).

(D) Brightfield representations of the growth of 500 cells per microwell over a 5 days period in a U-bottom microwell array. Aggregate growth is almost identical over the array. Thus, the platform of microwells according to the present invention displays a strong potential for high-throughput generation of monodisperse aggregates.

(E) If addition, aggregate loss upon medium change was assessed for the two platforms. No significant difference was observed. In average, less than 7% of the aggregates were lost upon medium change.

(F) Aggregate recovery from the platform was also assessed. No significant difference was observed. Close to 100% of the aggregates can be recovered. Finally, the maintenance of the main ESCs pluripotency marker Oct4 was analyzed by FACS everyday (data not shown).

At day 5 (G), still 99.0% of the cells express the marker, which is comparable to standard maintenance cultures.

Figure 15:
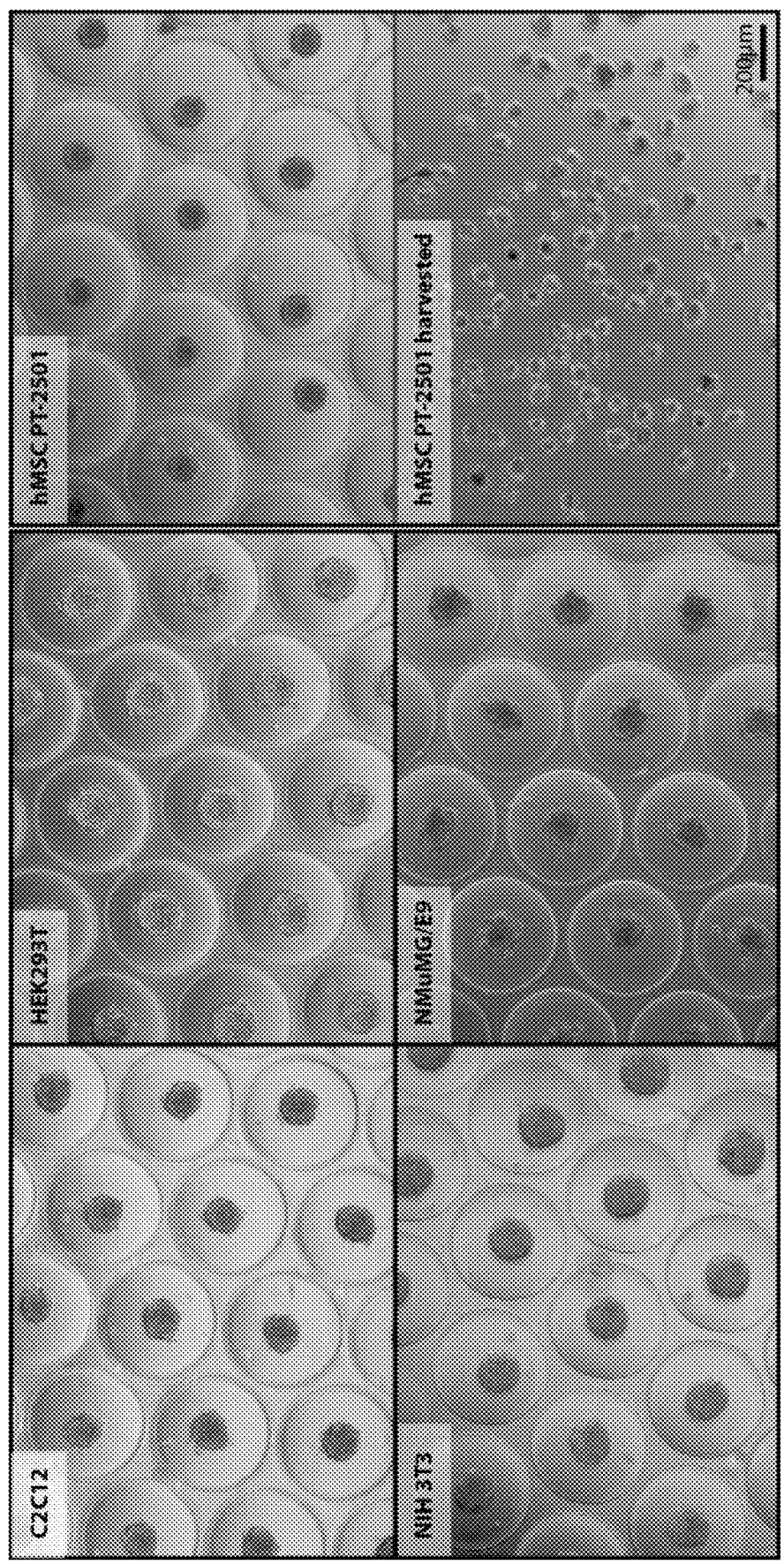
FIG. 15 illustrates an example of aggregation potential of varying cell types as indicated.

FIG. 15 illustrates an example of aggregation potential of varying cell types as indicated in the figure. Various cell types were seeded onto the U-bottom microwell assays according to the present invention. Brightfield representations of C2C12, HEK293T, NIH3T3 fibroblasts, NMuMG/E9 and human MSCs PT-2501 are shown. The different cell types successfully formed aggregates and could be maintained for 5 days. Also, they were all successfully harvested and kept clustered (data shown for hMSCs PT-2501 only, as a representative example). This high versatility of use demonstrates the strong potential of the microwells platform according to the present invention.

Figure 16:
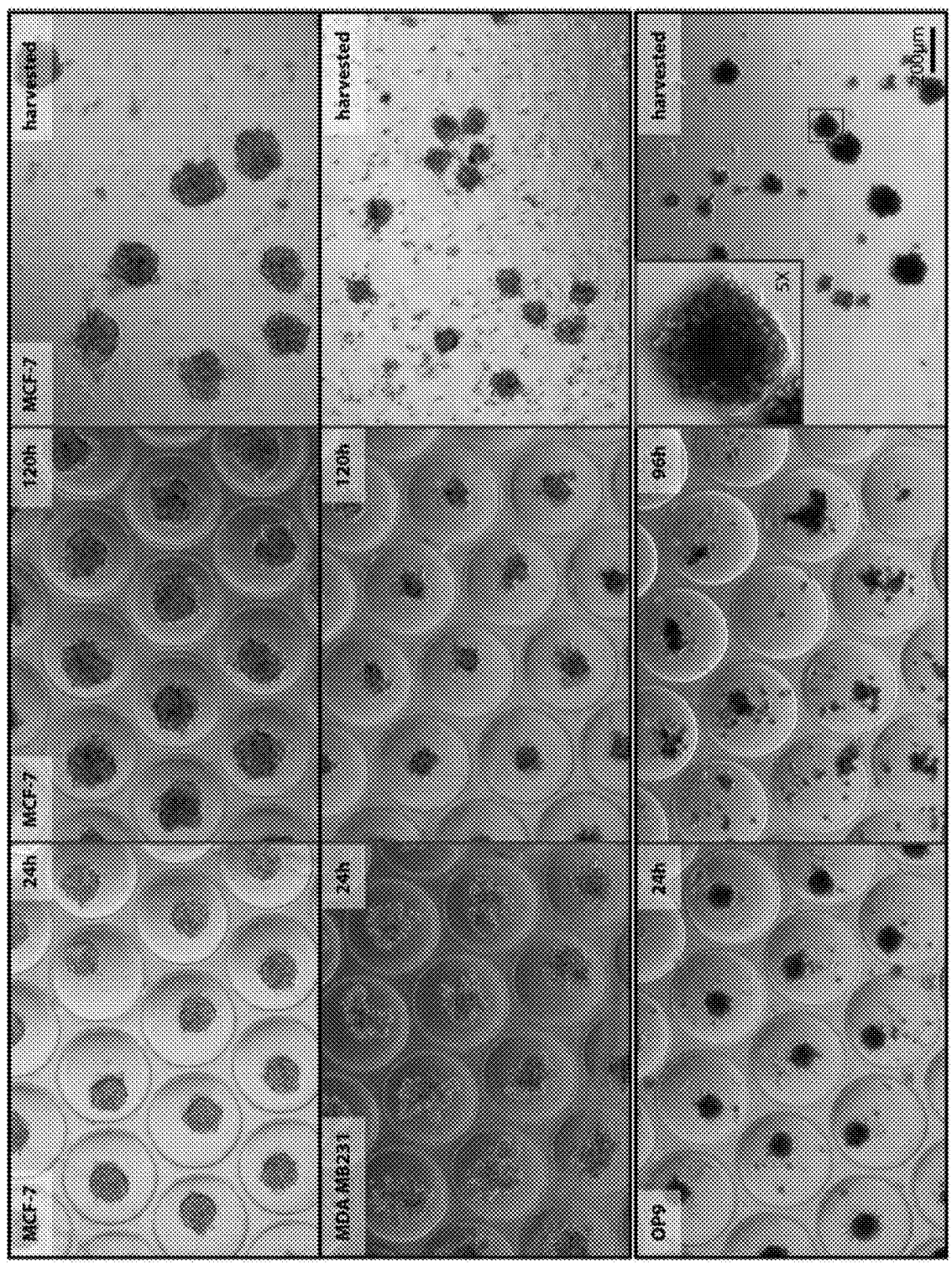
FIG. 16 illustrates example of aggregation potential of non-sphere forming cell types as indicated.

FIG. 16 illustrates an example for the aggregation potential of non-sphere forming cell types as indicated in the figure. Non-sphere forming cells were seeded onto U-bottom microwell arrays according to the present invention. Brightfield representations at different culture times of MCF-7, MDA-MB231 and OP9 as well as the corresponding harvested aggregates at day 5 are shown. The different cell types successfully formed aggregates and could be maintained for 5 days. Also, all three cell types were successfully harvested and kept clustered.

FIG. 17 (A) to (C) illustrates an example of three-dimensional culture format. (A) Perspective illustration of 3D encapsulated aggregates by sandwich casting of a second layer 6 of substrate, showing the potential of the technology according to the present invention to combine the localization of the aggregates in one single z-plane to enable encapsulated three-dimensional cultures.

(B) Illustration of the proof of concept of the sandwich casting. An first layer of U-bottom microwells 3 (400 µm diameter, 400 µm height and 40 µm pitch) is fabricated. PEG microbeads (≈200 µm diameter, G' 10-40 kPa) were captured in the microwells of this first layer my gravitational sedimentation to mimick cellular clusters. A second layer of PEG hydrogel was casted on top of the array to form a three-dimensional culture, completely encapsulating the PEG microbeads.

(C) Confocal representation of the sandwich casting approach. This demonstrates the potential of a platform according to the present invention to fabricate high throughput planar three-dimensional culture.

FIGS. 18 (A) to (F) and 18G illustrate a U-bottom microwell array according to the present invention with microfluidic integration through perfusable micrometer-scale channels.

Top view (A) and side cut view (B) of the schematic illustration of a U-bottom microwell 3 array according to the present invention with the integration of a microfluidic network for example comprising channels 15, 16 which are connected to respective inlets 15', 16' and outlets 15" and 16", see the perspective view in FIG. 18G.

The networks 5, 6 may be placed beneath the plane of the microwells 3 and aligned with it or not.

In a variant, there may be several independent networks next to each other or interconnected.

Figure 19:
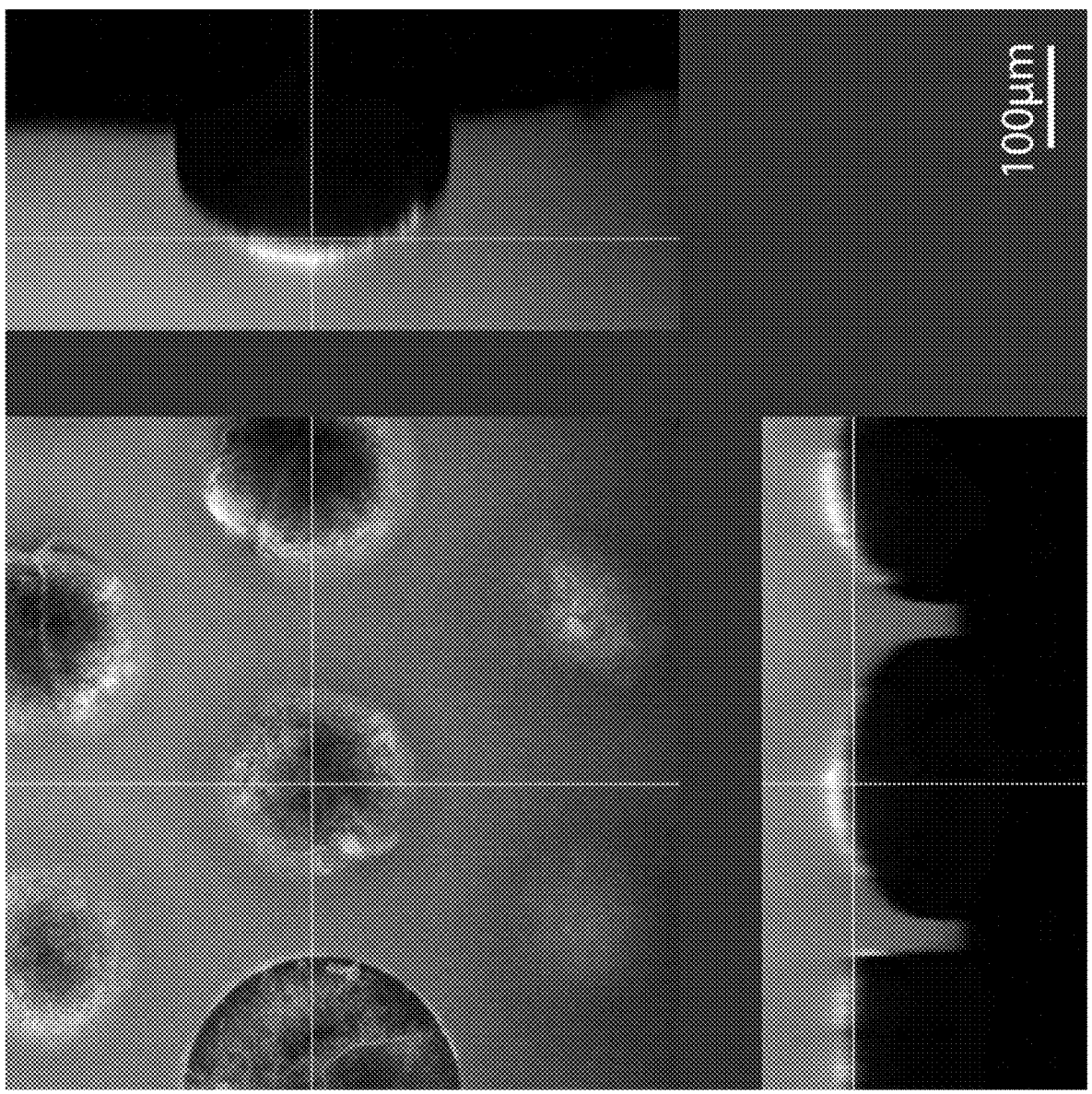
FIG. 19 illustrates an example of a bio-functionalization of the microwell bottom.

FIG. 19 illustrates an example of functionalization of the microwell bottom. Confocal representation of a U-bottom shaped microwell 3 (270 µm in diameter, 400 µm in height, 40 µm pitch). The bottom of the microwell 3 is functionalized with a model protein, here BSA.

Figure 20:
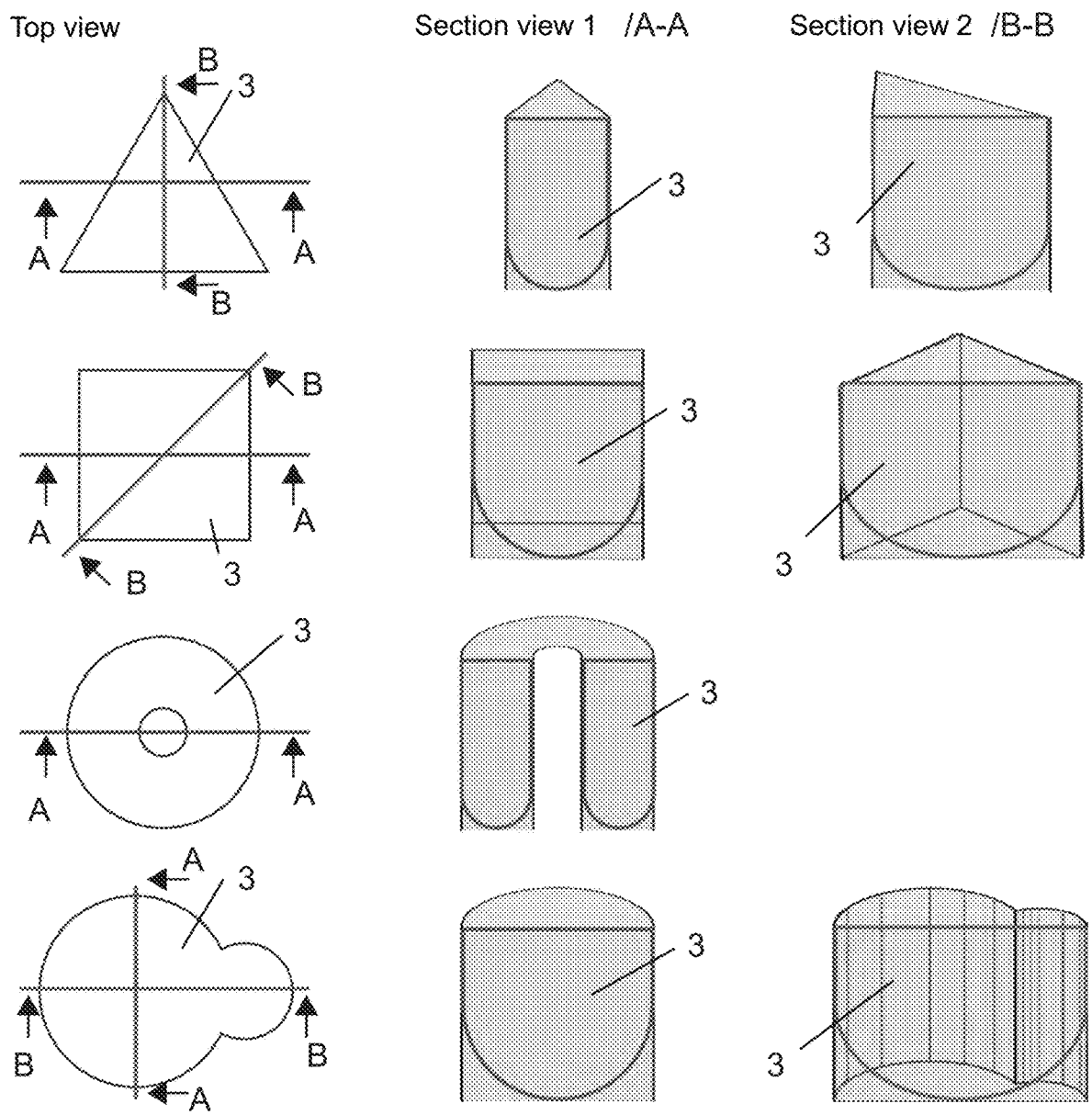
FIG. 20 illustrates examples of microwells in different shapes (top views and sectional views).

FIG. 20 illustrates examples of microwells 3 according to the present invention of different shapes. Schematic representation of microwells 3 having multiple geometrical shapes. Any shape, such as triangles, squares, toroids, and fully irregular structures can be used to produce U-bottom microwells with the above-discussed technique. These can be used for multiple applications; especially it can be a powerful tool for accessing the impact of the culture substrate geometry on cellular functions. FIG. 20 illustrates top views and section views along A-A and B-B.

Fabrication/Material and Methods

U-Bottom Microwell Array Fabrication

Using a Si Bosch process, flat-bottom microwells (here, cylindrical) of desired dimensions were etched into a silicon substrate. Then, a precise volume of a dilute liquid material, for example, polymers, such as the positive photoresist SU-8, was added into these wells using inkjet printing. Other deposition techniques can include, automated liquid dispensing, such as robotic liquid handling workstations, manual dispensing, such as pipetting, or any other type of deposition method. After evaporation, the material forms an evaporation meniscus, and creates a spherical bottom to form the U-shaped structures (see FIGS. 5 and 6). The material is finally solidified and used as a pattern for PDMS replica molding, which was then used as a molding pattern for the final substrate (e.g hydrogel). This replica molding process allows the replication of the silicon substrate geometry into the desired final substrate (see FIG. 7).

Microfabrication of U-bottom μwells 3 according to the present invention within each range of sizes using the above-mentioned approaches and values is very promising to create very high-density microwell arrays (see FIG. 4) for single cell culture and aggregate culture as shown in FIGS. 11 and 13-16.

Moldable Materials

Any kind of hydrogel (i.e., synthetic hydrogels as well as natural or naturally derived hydrogels) for example PEG, agarose, alginate, gelatin, collagen, matrigel, polymers such as PDMS, SU-8, etc . . . , plastics such as PMMA, PLA, PPA, PP, PE and so on, ceramics, metals, alloys, minerals, non metallic mineral, and glass.

Cell Culture

Oct4::GFP mouse embryonic stem cells (mESCs) provided by Austin Smith (University of Cambridge) were routinely expanded without feeders in Dulbecco's Modified Eagle Medium (DMEM) supplemented with leukemia inhibitory factor (LIF), ESC screened fetal bovine serum (FBS, Gibco) (15%) medium, non-essential amino acids (NEAA) sodium pyruvate (10 mM) and b-mercaptoethanol (0.1 mM), hereafter referred as ES cell medium (Smith 1991).

Human mesenchymal stem cells (hMSCs, PT-2501, Lonza) and OP9 murine stromal cells were routinely maintained in alpha-MEM supplemented with 10% FCS (Hyclone, batch AUA33984) and 1 ng/mL human FGF-2 (Peprotech).

NIH3T3 fibroblasts, MCF-7 human breast cancer cells, MDA-MB231 human breast cancer cells, C2C12 mouse myoblast cells, nMuMG E9 mouse breast cancer cells and human embryonic kidney (HEK) 293 cells were routinely maintained in DMEM supplemented with 10% fetal bovine serum (FBS), HEPES (10 mM) and sodium pyruvate (1 mM).

Aggregate Formation

The cells were detached with trypsin. A cell suspension with a density of interest was prepared (i.e. $3\times10^5$ cells/mL, $6\times10^4$ cells/mL, and 1000 cells/mL for achieving 500 cells/microwell, 100 cells/microwell and 1 cell/microwell, respectively) in the cell-type specific media. The U-bottom shaped microwell arrays were casted at the well bottom of 24-well plates and 2 mL of the prepared cell solution was added in the well. Cells settled down by gravitational sedimentation.

The cells were cultured for 5 days and the respective media was changed everyday.

Results/Applications and Examples

U-bottom microwells in various substrates and various sizes

U-bottom microwells 3 arrays 4 of different sizes (FIG. 8) were molded into a variety of cell culture compatible substrates including PDMS, PEG, agarose, gelatin, alginate and matrigel. To test the replicability in substrates at varying stiffness, the U-bottom microwells 3 arrays 4 were molded into PEG with polymer contents (w/v) ranging between 2.5% to 10% (FIG. 9). The lowest PEG stiffness castable was determined to be 150 Pa, equivalent to 2.5% PEG polymer content (as determined by rheology), below which architecture of the microwells 3 structure is no longer entirely guaranteed. The U-bottom microwells 3 can be efficiently reproduced in the aforementionned materials demonstrated by the preserved architecture (see FIG. 10).

Single Cell Expansion and Viability

Low cell densities, smaller than the number of were plated to maximize single cell distribution within the wells 3. Expansion and viability of single cells were quantified over the timeframe of five days every 24 hours (see FIG. 17D) between U-bottom microwells with a diameter of 400 μm in PEG (RBW PEG) and AggreWell™400 (AW PDMS). The survival rate of cultured single Oct4::eGFP ES cells significantly ($p<0.0001$) increases from 48.36%±31.74% on AW PDMS to 85.05%±8.51% on RBW PEG (see FIG. 17E). Further single cells cultured on RBW PEG grow to larger and more monodisperse aggregate populations after five days of expansion compared to AW PDMS (see FIG. 17F-G).

Limitations of the State-of-the-Art Commercial Platform

Aggregate sizes 24 h after seeding were compared between EBs generated in U-bottom microwells with diameters of 400 μm (see FIG. 12A-D) versus state-of-the-art AggreWells™400 (see FIG. 12 E-H). We observed that as opposed to U-bottom microwells the pyramidal shape of the AggreWells™ cavity lead to the generation of deformed EBs caused by the aggregates adapting the shape of the well (FIG. 3.4 A-C, black arrows). We also observed that at higher seeding densities (2000 and 3000 cells/EB) more robust spheroid formation was observed for U-bottom microwells compared to AggreWells™ (FIG. 12 C-D versus G-H), as demonstrated by the lower counts of floating cells in the supernatant (FIG. 12 L). Generally, EBs formed in U-bottom microwells displayed better indices of eccentricity (FIG. 12 I), form factor and compactness (FIG. 12 I-K). These results indicate that spheroid formation is generally enhanced in U-bottom microwells.

Further we observed that ES cells aggregated and cultured in Aggrewells™, frequently started to attach to the PDMS surface within less than 24 h (FIG. 12 M, N). The attached aggregates use the borders of sloped pyramidal microwells to crawl along the edges. This leads to the fusion of aggregates and the formation of more disperse spheroid populations.

Aggregate Size

U-bottom microwells 3 arrays 4 in 5% (w/v) PEG hydrogels were used to aggregate and culture Oct4::eGFP transgenic mouse ES cells. Initial aggregate size can be controlled by tuning the cell-seeding density. Densities of single cells, 100 cells per EB and 500 cells per EB were targeted. Aggregate sizes 24 h after seeding were determined and compared (see FIG. 13A-C). Single cells, 100 cells, 500 cells lead to EBs of 10-40 µm, 90-130 µm and 110-170 µm in diameter.

Aggregate Growth

Aggregate growth was quantified over the time course of five days from DBs of a starting density of 500 cells (see FIG. 14D) between U-bottom microwells with a diameter of 400 µm in PEG (RBW PEG) and AggreWell™400 (AW PDMS). The growth rate increases significantly (p<0.0001) after 48 h for RBW PEG (see FIG. 14A) Further, culturing 500 Oct4::eGFP cells per microwell leads to larger and more monodisperse final aggregate populations on RBW PEG compared to AW PDMS (see FIG. 14C-D).

Medium Change and Aggregate Recovery

Medium was exchanged both on AW PDMS and RBW PEG every 24 h for each of the five consecutive days by aspirating the complete volume of old medium and exchanging with the same amount through gentle pipetting at the side wall of the culture plate. The complete array surface was imaged after every medium change and aggregate loss was quantified. Aggregate loss for both AW PDMS and RBW PEG is well below 10% (see FIG. 14E).

Aggregates were recovered by pipetting up and down in the center of the well three times with complete liquid exchange each round and subsequently transferring the supernatant to a new culture plate. The complete array was imaged after this procedure to quantify aggregate recovery. Aggregate recovery for both AW PDMS and RBW PEG is close to 100% (see FIG. 14F). recovered aggregates can be used for other biological analyses. We determined the expression of Oct4 by cells dissociated from EBs cultured for five days on RBW PEG by flow cytometry. 99% of the cells retain their Oct4 expression after culture (see FIG. 14G).

Aggregation of Various Cell Types

U-bottom microwell arrays were molded in 5% (w/v) PEG hydrogels. Aggregates of various cell types were formed within these microwell arrays at a given starting density. C2C12, HEK293T, NIH3T3 fibroblasts, NMuMG clone E9 and human mesenchymal stem cells can efficiently form clusters on U-bottom microwells within 24 hours. The clusters are stable and can be efficiently harvested after culture, as demonstrated for human MSCs (FIG. 15).

U-bottom microwells 3 can be used to analyse cells that are inherently resistant to aggregation, as demonstrated by the non-spheroid forming cancer cell line MDA MB231. Within 24 hours the cells form loosely packed clusters, which compact further over the subsequent days in culture, so that even stable clusters can be retrieved from the microwells 3 arrays 4 after 120 hours (FIG. 16 top panel).

Mouse OP9 cells form stable clusters within 24 hours. Kept in culture in this conformation, the cells efficiently differentiate into adipocytes within three days also in the absence of exogenous adipogenic differentiation factors (Dexamethasone, IBMS and Insulin). Adipocyte clusters can be harvested from the microwell arrays at this point in time (see FIG. 16, bottom panel).

Planar 3D Encapsulation

U-bottom microwell arrays can be used for the planar 3D encapsulation of cells and spheroids to improve imaging quality and time consumption. As proof of concept we formed 5% (w/v) PEG-Alexa546 U-bottom microwell arrays. After polymerization, 200 µm 10% PEG-Alexa488 beads were distributed on top of the microwell arrays and left to settle into the cavities. The bead filled arrays were subsequently sealed with a second layer of 5% (w/v) PEG-Alexa647, completely encapsulating the beads in one focal plane in a 3D PEG environment (see FIG. 17).

Aggregate Microfluidics

In order to allow local and temporal biochemical manipulation of cell spheroids after formation without the need of transfer to a new culture plate, microfluidic channels were generated by micromolding below the plane of microwells 3 in close proximity (<500 µm distance) to ensure diffusion of the desired molecules within 24 h. As proof of principle FITC labeled high molecular weight (2000 kDa) dextran was perfused through channels beneath U-bottom microwell arrays. The dextran cannot perfuse through the hydrogel network, therefore efficiently and selectively labeling only the inside of the microfluidic channel (see FIG. 18).

Microwell Functionalization

U-bottom microwells 3 can be functionalized with different proteins according to previously described methods (Kobel et al. 2012). In brief, thin films of protein are formed on a hydrophilic glass slide on which a PDMS stamp is placed to allow adsorption of protein onto the PDMS surface. During the subsequent molding step of PEG, the protein is transferred to the hydrogel surface where it is incorporated into the hydrogel mesh through either static interactions or formation of covalent bonds. As proof of principle we used Alexa-647 labeled BSA to functionalize 5% (w/v) PEG-Alexa488 hydrogels (see FIG. 19).

Microwells of Different Shapes

With the presented technology, any shape U-bottom microwells 3 can be fabricated for specific applications (see FIG. 20). Indeed it has been shown that cells or cell aggregates function is strongly influenced by the geometry of their culture substrate. Thus, the presented microwells 3 array 4 has a high potential to answer how function is linked to geometry.

The examples, embodiments and process steps described in the present application are given by way of examples and should not be construed in a limiting manner.

Other variations are possible within the scope of the present invention by way of equivalent devices, materials and processes or steps. Also, the embodiments described herein may be combined as desired according to the circumstances.

The invention claimed is:

1. A device for aggregating cells, comprising:
a cavity,
wherein said cavity comprises a plurality of microwells for receiving at least one cell,
wherein each of said microwells comprises a vertical sidewall and a curved bottom,
wherein said microwells are made in a hydrogel layer,
wherein each of said microwells comprises a height of 200 µm to 3 mm,
wherein each of said microwells further comprises a diameter and an interwell distance between one microwell and another microwell,
wherein a ratio for said interwell distance to said diameter is less than or equal to 1/10, and
wherein said diameter of each of said microwells is 1 µm to 3 mm.

2. The device of claim 1, wherein said interwell distance between said plurality of microwells is minimal such that a cell, of said at least one cell, falling between said plurality of microwells will fall into one of said plurality of microwells and participate in aggregate formation.

3. The device of claim 1, wherein said interwell distance is 1 µm to 100 µm.

4. The device of claim 1, further comprising a microfluidic network of channels,
wherein said microfluidic network of channels is beneath a plane of said plurality of microwells.

5. The device of claim 4, wherein said microfluidic network of channels is aligned with said plurality of microwells.

6. The device of claim 5, wherein a distance between said microfluidic network of channels and a bottom portion of said plurality of microwells is less than 500 µm.

7. The device of claim 1, wherein said hydrogel layer is based on synthetic hydrophilic polymers, or naturally derived components or hybrids of synthetic polymers and naturally derived components.

8. The device of claim 7, wherein said synthetic hydrophilic polymer is poly(ethylene glycol), polyaliphatic polyurethanes, polyether polyurethanes, polyester polyurethanes, polyethylene copolymers, polyamides, polyvinyl alcohols, poly(ethylene oxide), polypropylene oxide, polyethylene glycol, polypropylene glycol, polytetramethylene oxide, polyvinyl pyrrolidone, polyacrylamide, poly(hydroxyl ethyl acrylate), poly(hydroxyethyl methacrylate), or mixtures thereof.

9. The device of claim 7, wherein said naturally derived components comprise polysaccharides, gelatinous proteins, and extracellular matrix (ECM) components comprising agarose, alginate, chitosan, dextran, gelatin, laminins, collagens, hyaluronan, fibrin or mixtures thereof, or complex tissue derived matrices.

10. The device of claim 1, wherein said hydrogel layer comprises a cross-linked hydrogel layer that is prepared by mixing and cross-linking at least two precursor components using a chemical reaction, wherein said at least two precursor components comprise a first precursor component comprising n nucleophilic groups and a second precursor component comprising m electrophilic groups, wherein n and m are at least two and the sum of n and m is at least five, and wherein said cross-linking is conducted between a first multi-arm polyethylene glycol (PEG) macromere, end-functionalized with nucleophilic thiol-groups, and a second multi-arm polyethylene glycol (PEG) macromere, end-functionalized with electrophilic vinylsulfone-groups at appropriate concentrations and conditions such as to allow for said cross-linked hydrogel layer to exhibit a shear modulus between 0.1 and 100 kPa.

11. The device of claim 10, wherein said hydrogel layer comprises an excess of free functional groups comprising nucleophilic groups, selected from the group consisting of amines and thiols, or electrophilic groups, selected from the group consisting of acrylates, methacrylates, acyl-amides, methacrylamides, acylonitiriles, quinones, vinyl-sulfones, maleimides and their derivates.

12. The device of claim 11, wherein said plurality of microwells is functionalized with biomolecules.

13. The device of claim 12, wherein said biomolecules are proteins, oligopeptides, oligonucleotides, or sugars.

14. The device of claim 13, wherein said proteins or oligopeptides are extracellular matrix (ECM)-derived or extracellular (EC)-mimetics and attached to:
said nucleophilic groups;
said electrophilic groups; or
said thiol-groups of said first multi-arm polyethylene glycol (PEG) macromere, using a heterobifunctional linker,
wherein a first functional group of said heterobifunctional linker is reactive to said functional groups attached to termini of said hydrophilic polymer and a second functional group of said heterobifunctional linker, and
wherein said heterobifunctional linker comprises succinimidyl active ester that is capable of non-specifically tethering to one or more of said biomolecules of interest via amine groups of said succinimidyl active ester.

15. The device of claim 12, wherein said biomolecules are tagged such as to be tethered to said hydrogel layer by affinity.

16. The device of claim 15, wherein said biomolecules have tags to enable binding to targets, wherein said targets comprise ProteinA, ProteinG, Protein A/G, Streptavidin, NeutrAvidin, antibodies, S-fragment of RNaseA, calmodulin, cellulose, chitin, glutathione, amylose, or functionalized oligopeptides and oligonucleotides having said nucleophilic groups or said electrophilic groups that can react with said functional groups on said hydrogel layer.

17. The device of claim 1, wherein said height is greater than or equal to said diameter.

18. The device of claim 1, wherein said height is greater than said interwell distance.

19. A device for aggregating cells, comprising:
a plurality of cavities;
a hydrogel layer; and
a plurality of microwells disposed in each of the plurality of cavities, the plurality of microwells each configured to receive a cell, the plurality of microwells each comprising:
a vertical sidewall; and
a curved bottom,
wherein each of the plurality of microwells has a diameter, a height and an inter-well distance between one microwell and another microwell which are configured independently from each other,
wherein said plurality of microwells are made in said hydrogel layer,
wherein a ratio for said interwell distance to said diameter is less than or equal to $1/10$, and
wherein said diameter of each of said microwells is 1 µm to 3 mm.

* * * * *